(12) United States Patent
Cernasov

(10) Patent No.: US 7,652,273 B2
(45) Date of Patent: Jan. 26, 2010

(54) RADIATION ATTENUATION DEVICE AND METHOD INCLUDES RADIATION ATTENUATING FLUID AND DIRECTLY COMMUNICATING ADJACENT CHAMBERS

(76) Inventor: Andrei Cernasov, 86 Miller La., Ringwood, NJ (US) 07456

( * ) Notice: Subject to any disclaimer, the term of this patent is extended or adjusted under 35 U.S.C. 154(b) by 248 days.

(21) Appl. No.: 11/780,896

(22) Filed: Jul. 20, 2007

(65) Prior Publication Data
US 2008/0048135 A1    Feb. 28, 2008

Related U.S. Application Data

(60) Provisional application No. 60/807,988, filed on Jul. 21, 2006.

(51) Int. Cl.
*G21F 3/00* (2006.01)
(52) U.S. Cl. .................. 250/515.1; 250/505.1; 378/156; 378/157; 378/158
(58) Field of Classification Search ............. 250/505.1, 250/506.1, 507.1, 515.1, 519.1, 518.1; 359/237; 378/65, 67, 150, 151, 156, 157, 158, 159, 378/16, 155
See application file for complete search history.

(56) References Cited

U.S. PATENT DOCUMENTS

| | | | |
|---|---|---|---|
| 6,201,852 | B1 | 3/2001 | Goddu et al. |
| 2003/0198319 | A1* | 10/2003 | Toth et al. .................... 378/159 |
| 2004/0105525 | A1* | 6/2004 | Short et al. ................ 378/98.8 |
| 2007/0040127 | A1* | 2/2007 | Brahme et al. .............. 250/389 |
| 2007/0064871 | A1 | 3/2007 | Earl et al. |
| 2007/0092066 | A1 | 4/2007 | Tkaczyk et al. |
| 2007/0176079 | A1* | 8/2007 | Wany ...................... 250/208.1 |

OTHER PUBLICATIONS

International Search Report of International Application No. PCT/US07/74004 mailed Mar. 24, 2008.

* cited by examiner

*Primary Examiner*—Nikita Wells
*Assistant Examiner*—Nicole Ippolito Rausch
(74) *Attorney, Agent, or Firm*—Lowe Hauptman Ham & Berner, LLP

(57) ABSTRACT

An apparatus and method of attenuating radiation includes oscillating at least one fluid having a radiation attenuating property between at least two chambers, incident to applied radiation. The radiation attenuating device includes at least two communicating adjacent chambers, at least one fluid having radiation attenuating properties moveable between the at least two chambers, and a control circuit configured to oscillate the at least one fluid between the chambers.

24 Claims, 20 Drawing Sheets

RADIATION ATTENUATION DEVICE AND METHOD INCLUDES RADIATION ATTENUATING FLUID AND DIRECTLY COMMUNICATING ADJACENT CHAMBERS

CROSS-REFERENCE TO RELATED APPLICATION

This application claims the benefit of U.S. Provisional Patent Application Ser. No. 60/807,988 filed Jul. 21, 2006, entitled "Radiation Attenuating Device," herein incorporated by reference in its entirety.

FIELD

Embodiments of the invention relate to medical devices using radiation sources and, more particularly, relate to configurable radiation collimators.

BACKGROUND OF THE INVENTION

During 2005, US doctors performed a record 180 million X-ray assisted procedures and, worldwide the number surpassed 2.5 billion. Over 500 million square meters of human tissue is exposed annually to artificially generated X-rays.

Although the health benefits are undeniable, the growing use of X-rays is also responsible for a dramatic increase in a number of related ailments. X-rays can damage cell structures with immediate or delayed consequences. Most serious of all are the 30,000 new cases of radiation induced cancers diagnosed every year, 5700 in the US alone. Of particular concern is fluoroscopy where the incidence of fatal cancers may be as high as 1 per 1000 exposures.

The amount of radiation to which a patient is exposed depends on a number of factors, including the sensitivity of the radiation detector used and the amount of visual information necessary to successfully perform the procedure.

The sensitivity of the radiation detector is determined by the current state of technology. The industry is moving toward a film-free infrastructure where X-ray films are replaced by amorphous silicon detector arrays and images are enhanced and archived digitally. Although digital systems are more convenient, the resolution of the digital systems lags behind that of X-ray film.

To accommodate the requirements of various medical procedures, the information obtained from the areas of interest requires the maximum resolution possible while, at the same time, exposing the patient to a minimum amount of radiation. Because all known X-ray sources generate an essentially uniform output beam, health care providers may use specially shaped shields to cover parts of the patient's body (and their own), while exposing the areas of interest to the X-ray beam. These shields are generally made of lead and are manufactured prior to the procedure.

SUMMARY

Apparatus and methods are herein described to modulate radiation by dynamically shielding selected areas thereby preventing the overexposure of tissue.

A method of attenuating radiation includes oscillating at least one fluid having a radiation attenuating property between at least two chambers in a radiation attenuating element, wherein the applied radiation is incident to the chambers of the element.

Further disclosed is a radiation attenuating device that performs the method described above, including at least two communicating adjacent chambers, at least one communication channel connecting the chambers, a radiation attenuating fluid moveable between the chambers, and a control circuit configured to oscillate the radiation attenuating fluid between the chambers.

In addition, a radiation imaging system is describe, wherein the system is configured to dynamically modulate an amount of radiation incident to a target to be radiated. The system comprises: a radiation source, a radiation shield further comprising a plurality of radiation attenuating devices, each radiation attenuating device comprising a dynamically configurable radiation attenuating property, and a control unit configured to generate at least one control signal to each radiation attenuating device.

BRIEF DESCRIPTION OF THE DRAWINGS

Embodiments of the present invention are illustrated by way of example, and not by limitation, in the figures of the accompanying drawings, wherein elements having the same reference numeral designations represent like elements throughout and wherein.

DETAILED DESCRIPTION

Figure 1:
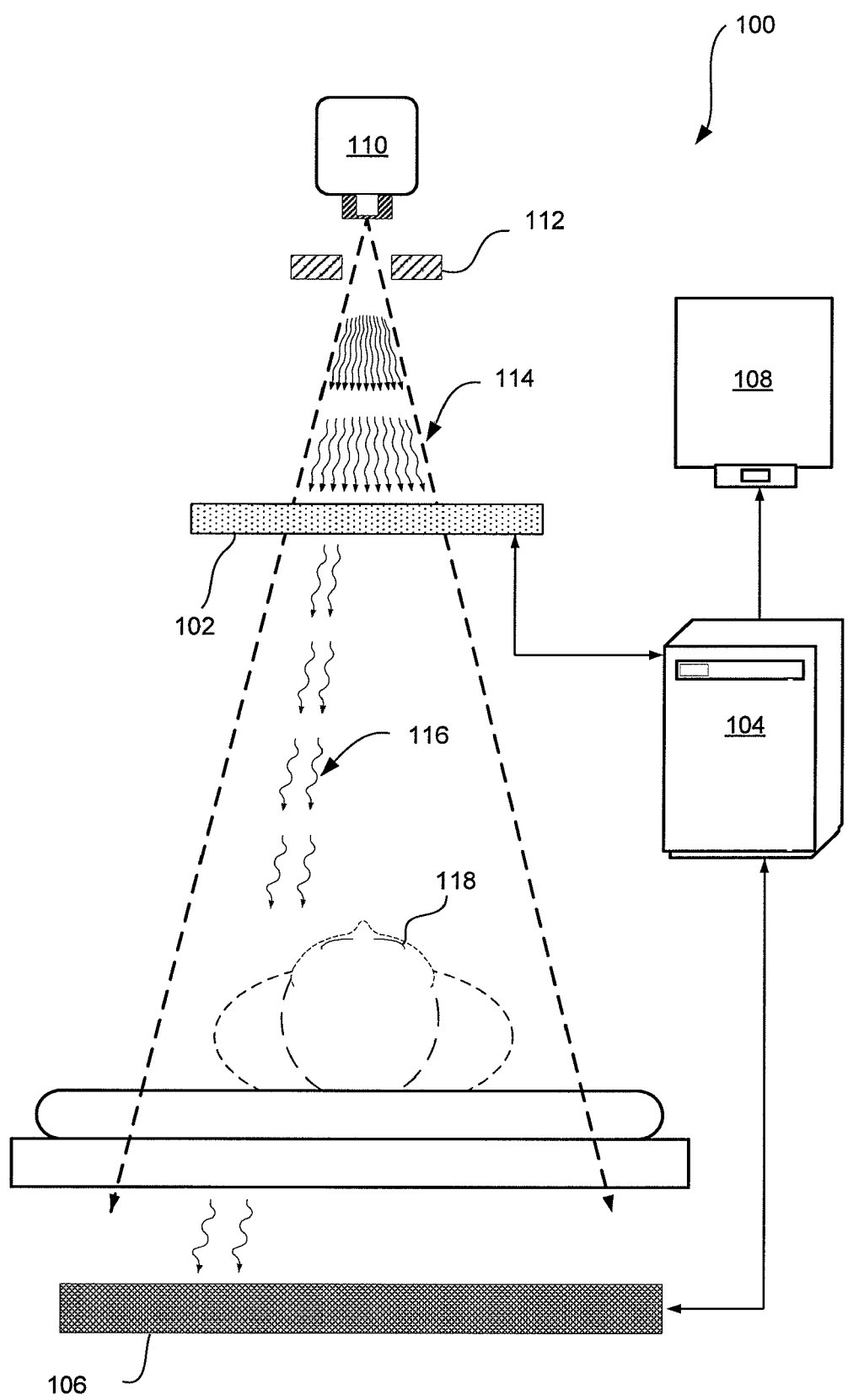
FIG. 1 is one embodiment of a X-ray diagnostic system.

FIG. 1 illustrates a radiation imaging system 100 that dynamically adjusts a radiation attenuation property of a radiation shield 102 in order to shield predetermined areas of a target from radiation, thereby preventing unnecessary overexposure of tissues. In one embodiment, system 100 comprises a radiation source 110, a collimator 112, a programmable radiation attenuating device, hereinafter "radiation shield" 102, a radiation detector array 106, a control unit 104, and a display element 108.

In operation, radiation 114 emitted by radiation source 110, passes through collimator 112 and is incident upon radiation shield 102. Control unit 104 operates to dynamically configure radiation shield 102 to pass a predetermined amount of the incident radiation 114 through selected areas of radiation shield 102, thereby controlling an amount of pass-through radiation 116 incident upon a selected area of a target, such as patient 118. Detector array 106 detects the amount of pass-through radiation 116 not absorbed by the target. In one embodiment, detector array 106 is an active electronic array that is in communication with control unit 104. In another embodiment, array 106 is photographic film that is exposed by radiation 116.

Based upon the detected radiation, control unit 104 displays an image on display device 108. Furthermore, in at least one embodiment, control unit 104 reconfigures the modulation properties of radiation shield 102 based upon the signals received from detector array 106.

Figure 2:
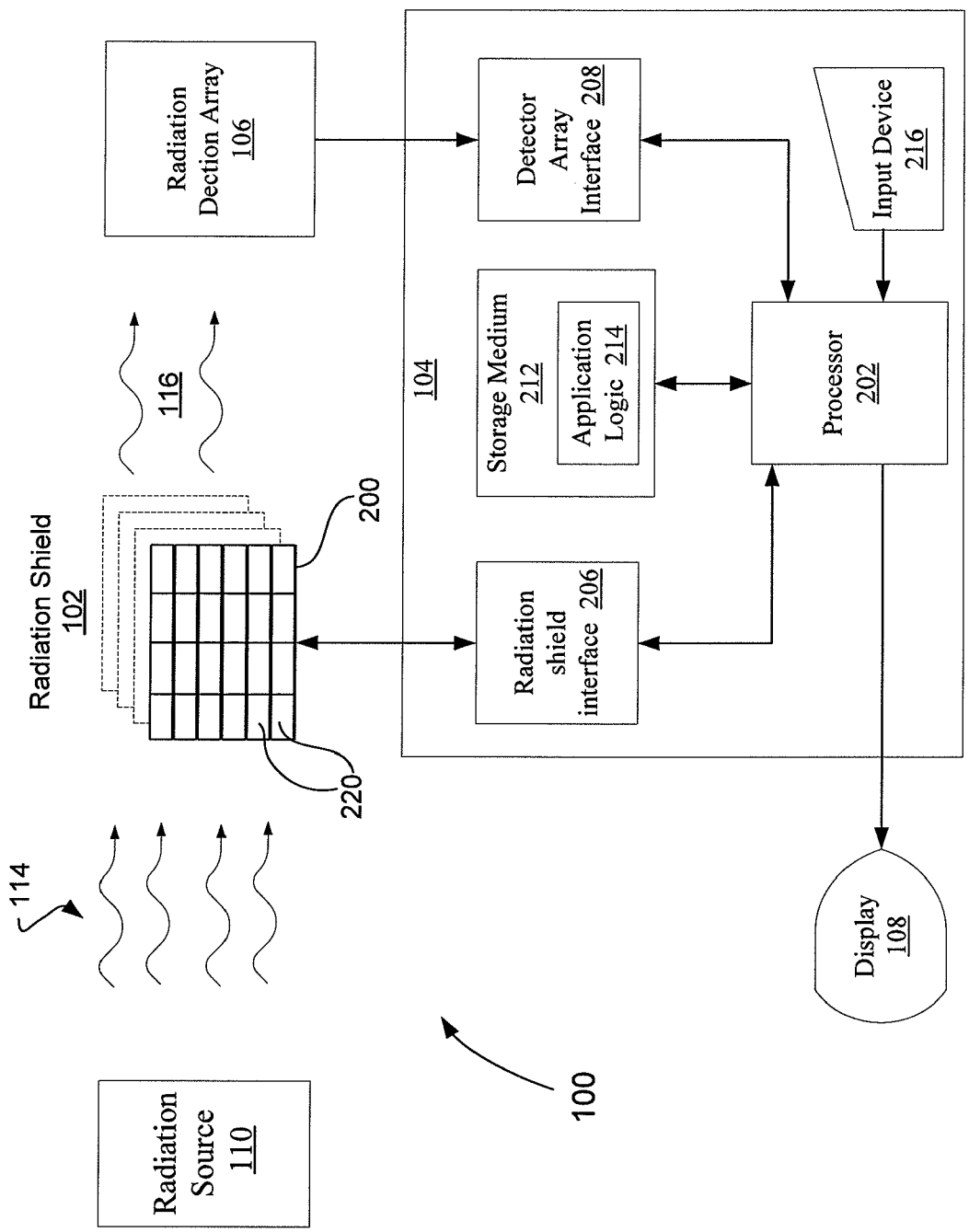
FIG. 2 is a block diagram of one embodiment according to FIG. 1.

FIG. 2 illustrates one embodiment of a block diagram according to the system in FIG. 1. In one embodiment, control unit 104 is a computerized device, such as a portable computer, personal computer, or any computerized device capable of providing input to a radiation shield 102, receiving input from radiation detector array 106, and displaying screen images on display 108.

In one embodiment, control unit 104 comprises processor 202 and a storage medium 212 that may comprise: RAM memory, flash memory, ROM memory, EPROM memory, EEPROM memory, registers, a hard disk, a removable disk, a CD-ROM, or any other form of storage medium known in the art. An exemplary storage medium may be coupled to processor 202, such that processor 202 can read information from, and write information to, storage medium 212. In the alternative, storage medium 212 may be integral to processor 202. Further, in some aspects, processor 202 and storage medium 212 may reside in an ASIC. Additionally, the ASIC may reside in a user terminal. In the alternative, processor 202 and storage medium 212 may reside as discrete components in a user terminal. Additionally, in some aspects, the steps and/or actions of a method or logic may reside as one or any combination or set of instructions on a machine readable medium and/or computer readable medium.

Control unit 104 further comprises an interface, i.e., shield interface 206, between radiation shield 102 and processor 202. Non-limiting, in at least one embodiment, shield interface 206 is a serial interface, such as provided by a universal serial bus (USB) connection, a parallel interface, or any known interface that is operable to allow control unit 104 to transmit signals that dynamically adjust the radiation attenuating properties of radiation shield 102.

Similarly, detector array 106 transmits information to processor 202 pertaining to the amount of radiation incident to the detector array 106 using detector array interface 208.

An input device 216 allows an operator to control operation of the radiation imaging system 100 and may comprise one or more input devices, such as a key or a keyboard, a mouse, a touch-screen display, and a voice recognition module. In other embodiments, input device 216 includes an interface to a computer network, allowing a user to operate system 100, including radiation shield 102, from a remote location.

An output mechanism may comprise display 108, an audio speaker, and/or a haptic feedback mechanism, for example, for relaying information to the user of system 100. For example, display 108 displays data from detector array 106 processed by processor 202, user menus, configuration settings, and real time status of the radiation imaging system 100.

Application logic 214, embodied in a software module residing in storage medium 212 and executable by processor 202, operates to dynamically vary the radiation attenuating properties of radiation shield 102. Application logic 214 may be loaded into storage medium 212 via various media, including, but not limited to a compact disk (CD) or universal serial bus (USB) storage components with the application software stored thereon, and an Internet connection from which logic 214 may be downloaded from a remote server.

Figure 3:
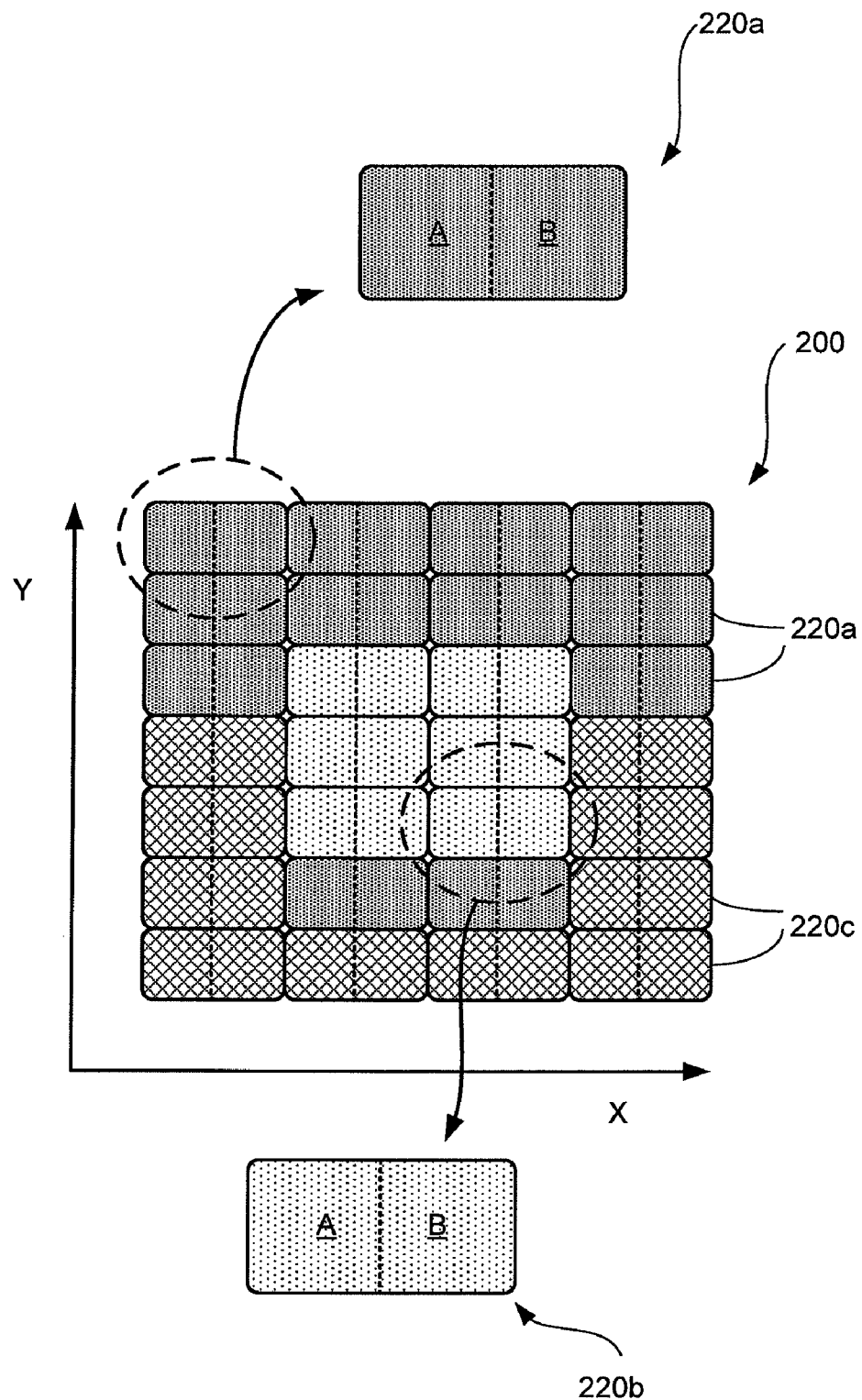
FIG. 3 illustrates a top view of an embodiment of a radiation shield having adjacent attenuating element cells arranged in a two dimensional structure.

As illustrated in FIG. 2, radiation shield 102 comprises at least one planar attenuating array 200 in an x-y plane, comprising a plurality of adjacent attenuating elements 220. FIG. 3 illustrates a portion of attenuating array 200, wherein each of the plurality of attenuating elements 220 comprises at least two chambers (A and B) enclosing a radiation attenuating fluid. Each attenuating element 220, e.g., 220a, 220b, and 220c, is individually and dynamically programmed to provide a predetermined attenuation property from a minimum of roughly 50% to a maximum approaching 100% of the incident radiation 114, based upon a predetermined amount of desired radiation to be absorbed by a target.

Two non-limiting embodiments of attenuating element 220 are herein disclosed. FIGS. 4A-4I disclose an attenuating element 402 comprising radiation attenuating fluid 408 that, under control of control unit 104, is moved between two communicating chambers to block up to almost 100% of incident radiation 114.

A second embodiment of attenuating element 220 is illustrated in FIGS. 7-15, wherein a plurality of attenuating elements 804 are stacked in a z-axis, wherein the amount of incident radiation 114 that is blocked is based upon the total amount of radiation attenuating fluid stacked in the z axis at any one time.

The amount of attenuating fluid required to block a desired amount of radiation is based upon physical laws known to those knowledgeable in the field of diagnostic radiation. When a homogeneous layer of a certain predetermined thickness x is exposed to an incident radiation of uniform intensity $I_0(t)$ the layer attenuates the incoming radiation according to the Beer-Lambert Law:

$$I(x, t) = I_0(t)e^{-\mu x}$$

where μ is the absorption coefficient of the material and x is its thickness.

As illustrated in FIG. 1, radiation imaging system 100 is operable to project patterned transmitted radiation 116 towards a target 118. Radiation shield 102 allows varying degrees of incident radiation 114 to pass through radiation shield 102 by varying the attenuation property of each of the plurality of attenuating elements 220. Although dynamic adjustment of radiation shield 102 takes a finite amount of time, the time to perform the adjustments is generally shorter than the exposure time.

Radiation shield 102 comprises a large number of individual attenuating elements 402 or 804, wherein the x and y dimensions of each element is dependent upon several factors, including: the number of independently controlled attenuation elements, and their distance from the radiation source. Accordingly, dimensions x and y range from, but are not be limited to, 0.1 mm to 10 mm. Pattern adjustment is quickly achieved by oscillating small amounts of radiation attenuating fluid between adjacent chambers A and B of each element, whether radiation shield 102 is comprised of a single array of adjacent attenuating elements 402, or a stacked array of attenuating elements 804. The principles described herein may be applied to other designs usable with radiation other than X-rays, the designs having different groupings of different numbers of chambers, each chamber having different numbers of movable shields.

Figure 4A:
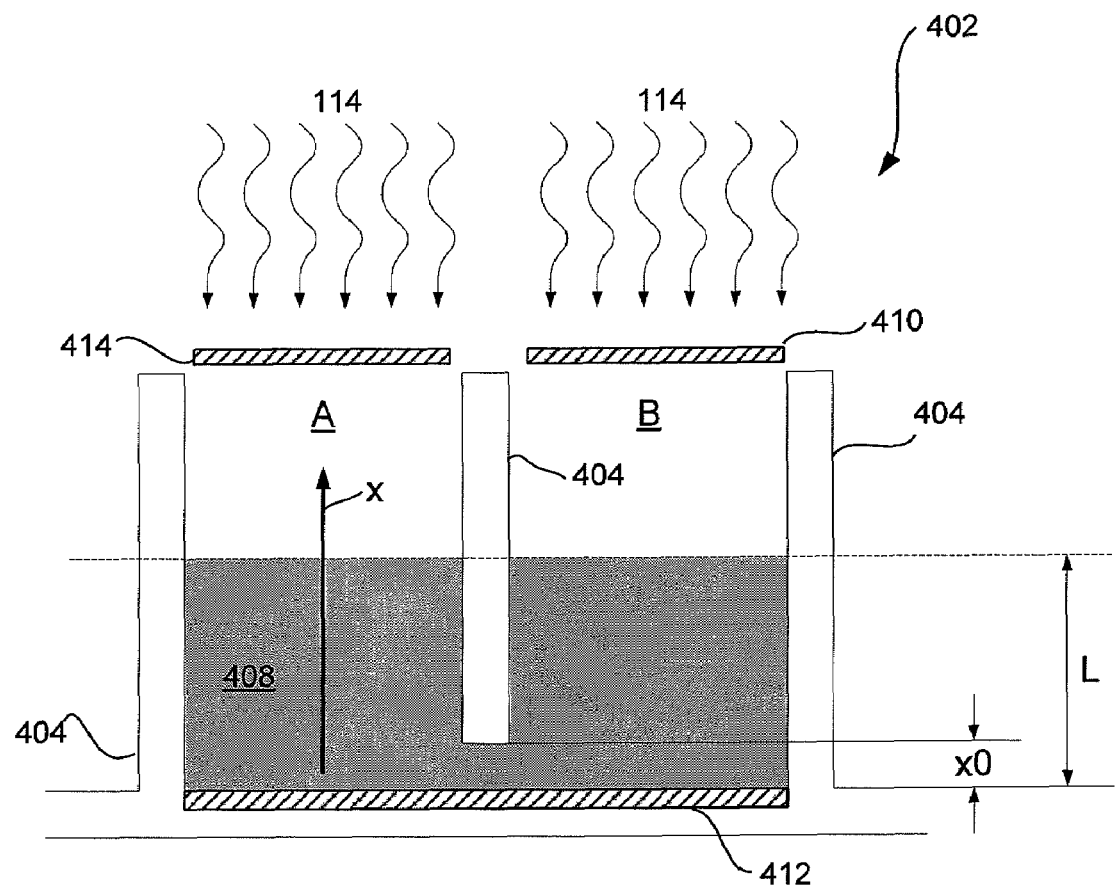
FIGS. 4A-4C illustrates various operational states of an embodiment of a radiation attenuating element comprising a moveable radiation shield fluid.
Figure 4B:
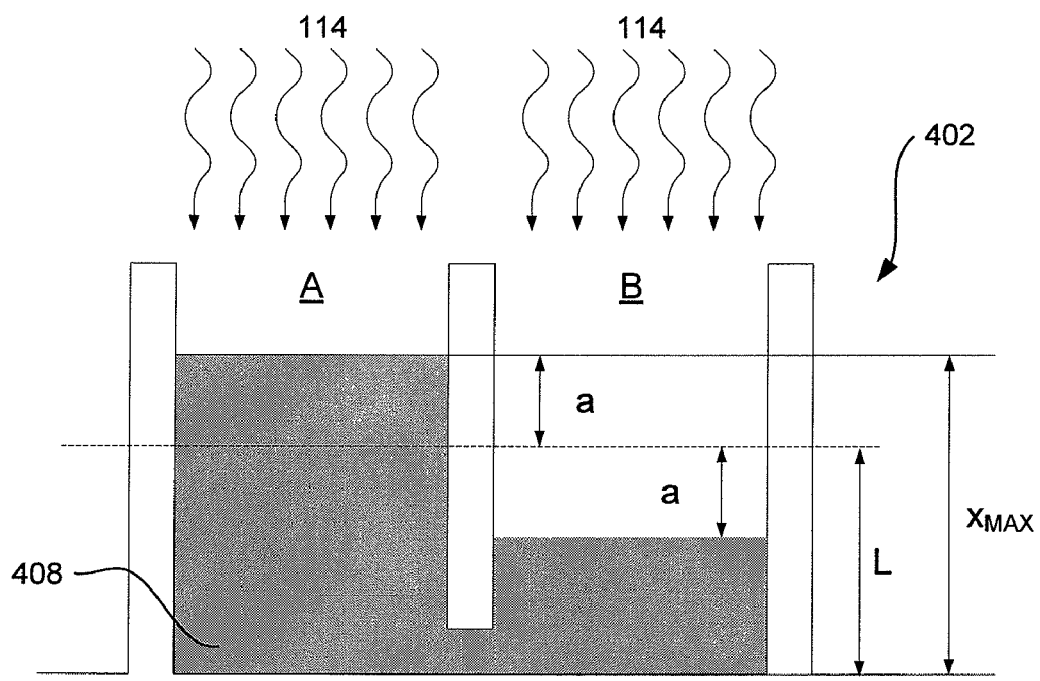
Figure 4C:
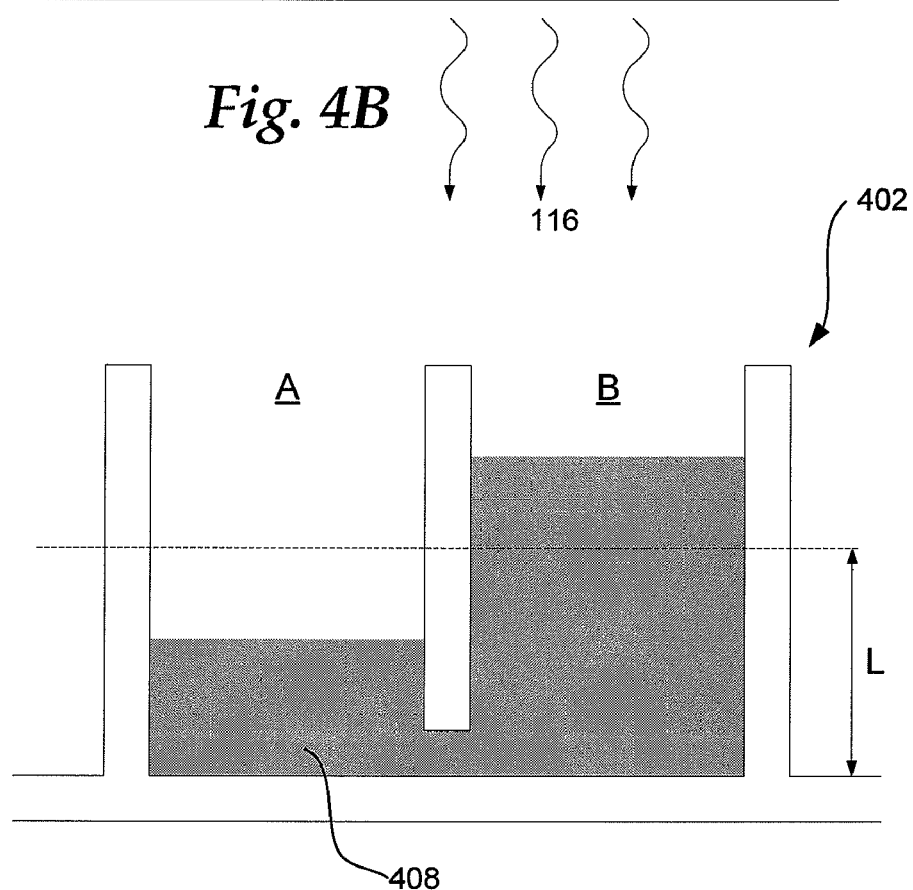

FIGS. 4A-4C illustrate various operational states of one embodiment of attenuating element 402 that includes a two chamber (A and B) communicating structure partially filled with a fluid 408 comprising a property of attenuating radiation. Attenuating element 402 is formed of a glass, silicon, plastic, or other radiation transmitting material 404 that depends upon the size of the element 402, which is further determined by the specific application. Fluid 408 may be mercury or liquid compounds of iodine, thallium, and any other liquid or suspension that exhibits radiation attenuating properties.

Chambers A and B contain structures capable of exerting force on the working fluid. These structures may generate electric, magnetic, electro-phoretic, dielectro-phoretic, electro-wetting, magneto-hydro-dynamic, or other forces on the working fluid. For example, FIG. 4A illustrates radiation transparent electrodes 410, 412, and 414 that shift electrically conductive attenuating fluid 408 between chambers A and B based upon capacitance. Because fluid 408 is in electrical contact with electrode 412, a voltage applied between electrodes 414 and 412 causes electrode 414 to attract fluid 408 into chamber A. Similarly, application of a voltage between electrodes 410 and 412 causes electrode 410 to attract fluid 408 into chamber B.

To facilitate a better understanding of the operation of a typical attenuating element 402, FIGS. 4A, 4B, and 4C illustrate an element 402 exhibiting only two different radiation attenuating configurations. FIG. 4A illustrates fluid 408 at rest, with fluid 408 at equal heights L in both chambers A, B which provides maximum average attenuation of the incident radiation. FIGS. 4B, 4C illustrate attenuating element 402 under the effect of the mentioned driving forces, wherein fluid 408 oscillates between the two predetermined states with different fluid heights. For example, in FIG. 4B, the height of fluid 408 in chamber A is raised to a height L+a, while in chamber B, the height drops to L−a. In FIG. 4C, the height of fluid 408 in chamber A drops to L−a, while in chamber B, the height is raised to L+a.

The time it takes to switch between configurations of FIG. 4B and FIG. 4C is assumed to be negligible compared to the exposure time and within a single exposure the working fluid 408 is either at rest, i.e., FIG. 4A, or oscillates a large number of times between the states shown in FIG. 4B and 4C. The radiation passing through chamber A during each state is given by:

$$I_{Rest} = I_0 e^{-\mu L} \quad \text{(FIG. 4A)}$$

$$I_{High} = I_0 e^{-\mu [L+a]} \quad \text{(FIG. 4B)}$$

$$I_{Low} = I_0 e^{-\mu [L-a]} \quad \text{(FIG. 4C)}$$

Whereas the radiation passing through chamber B is given by:

$$I_{Rest} = I_0 e^{-\mu L} \quad \text{(FIG. 4A)}$$

$$I_{High} = I_0 e^{-\mu [L+a]} \quad \text{(FIG. 4C)}$$

$$I_{Low} = I_0 e^{-\mu [L-a]} \quad \text{(FIG. 4B)}$$

When the fluid undergoes oscillations, the ratio of the average intensity of pass-through radiation 116 divided by the transmitted intensity when the working fluid is at rest, is known as the average relative attenuation ($A_R(a)$), and is determined by:

$$A_R(a) = \frac{I_{High} + I_{Low}}{2 I_{Rest}}$$
$$= \frac{e^{-\mu[L+a]} + e^{-\mu[L-a]}}{2 e^{-\mu L}}$$
$$= \frac{e^{-\mu a} + e^{\mu a}}{2}$$
$$= \cosh(\mu a)$$

Figure 5:
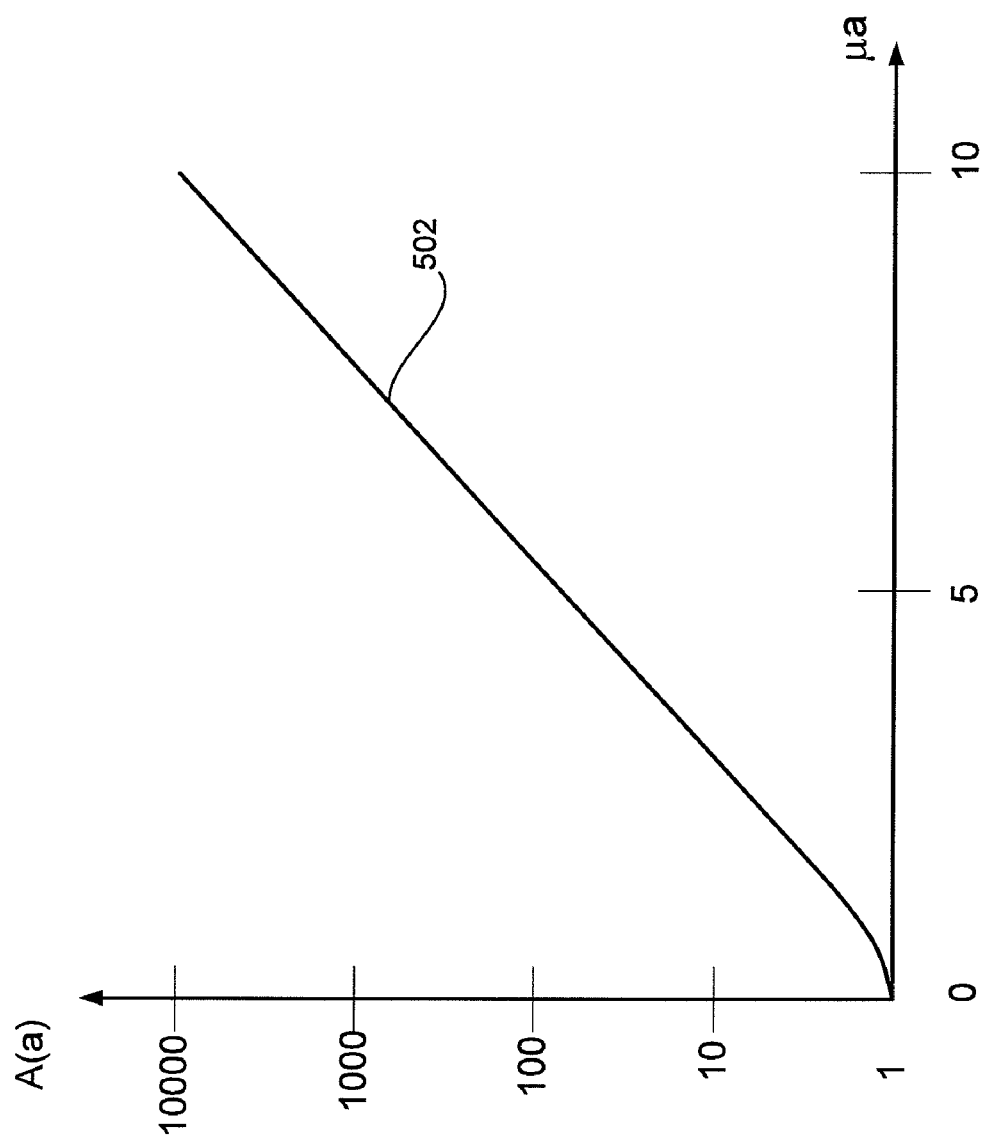
FIG. 5 is a graph of the ratio of average intensity based upon the amount of radiation shielding fluid.

As can be seen in FIG. 5, the amount of transmitted radiation is a function (502) of the oscillation amplitude of the fluid 408. The higher the amplitude of the oscillation, the higher the transmitted radiation intensity A(a), wherein the transmitted intensity during oscillations is orders of magnitude larger than when the fluid is at rest.

The more relevant absolute attenuation coefficient A is defined as the ratio of the transmitted radiation intensity divided by the intensity of the incident beam:

$$A(a) = \frac{I_{Av}}{I_0} = \frac{e^{-\mu[L+a]} + e^{-\mu[L-a]}}{2} = \frac{e^{-\mu L - \mu a} + e^{-\mu L + \mu a}}{2}$$

Making the change in variables $x = \mu L$, $y = a/L$:

$$A(a) = \frac{e^{-x-xy} + e^{-x+xy}}{2} = \frac{e^{-xy} + e^{-xy}}{2} = e^{-x} \cosh(xy)$$

Figure 6:
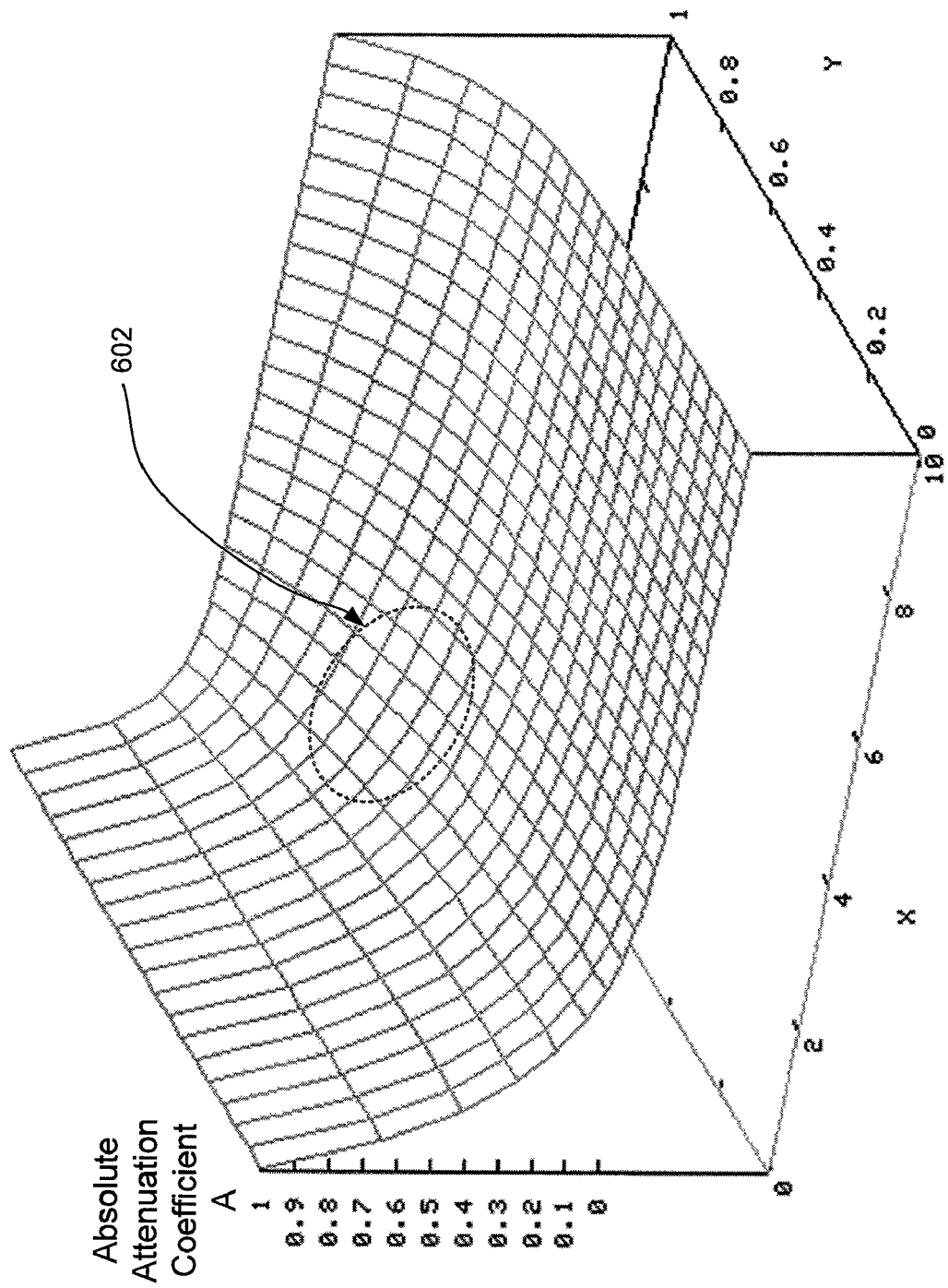
FIG. 6 is a graph of radiation attenuation as a derived function of shield composition and geometry.

FIG. 6 illustrates a graph of A as a function of x and y, and indicates that A is strongly dependent on the relative amplitude of the oscillation a/L as well as on the amount and nature of the working fluid $\mu L$.

In the limit when a/L=y=1:

$$A(L) = \frac{e^{-2x} + 1}{2}$$

When $\mu L = x$ is large and the level of fluid 408 is low, the absolute attenuation is 0.5. The transparency of element 402 to the incident radiation 114 is at its maximum value of about 50%. When $\mu L = x$ is large and the fluid level is high, the absolute attenuation approaches 1 (100%), blocking almost all the incident radiation 114.

As the oscillation frequency increases, the inertial forces of fluid 408 forces the fluid into a harmonic motion which can be described by:

$$x(t) = L + a \sin(\omega t)$$

$$\omega = 2\pi f = 2\pi/T$$

Where $\omega$ is the angular frequency, f the frequency, and T the period of the motion. Then:

$$I(x,t) = I_0 e^{-\mu x(t)}$$

$$I(x,t) = I_0 e^{-\mu [L + a \sin(\omega t)]}$$

The average intensity of the pass through radiation 116 is given by:

$$I_{AV}(a) = \frac{1}{T}\int_0^T I_0 e^{-\mu[L+a\sin(\omega t)]} dt$$

$$I_{AV}(a) = \frac{I_0 e^{-\mu L}}{T}\int_0^T e^{-\mu a \sin(2\pi t/T)} dt$$

Making the change of variable:

$$\tau = 2\pi t/T$$

$$dt = (T/2\pi)d\tau$$

We successively find:

$$I_{AV}(a) = \frac{I_0 e^{-\mu L}}{2\pi}\int_0^{2\pi} e^{-\mu a \sin(\tau)} dt$$

$$I_{AV}(0) = I_{AV0} = I_0 e^{-\mu L}$$

The equation for the average relative attenuation is then:

$$A_R(a) = \frac{I_{AV}(a)}{I_{AV0}} = \frac{1}{2\pi}\int_0^{2\pi} e^{-\mu a \sin(\tau)} d\tau$$

Numerical evaluation of this equation yields the results shown in TABLE 1, indicating that given large enough values of μa, the relative attenuation A(a) can be substantial.

TABLE 1

| | μa | | | | | | |
|---|---|---|---|---|---|---|---|
| | 0.1 | 0.2 | 0.5 | 1 | 2 | 3 | 4 |
| A(a) | 1.002502 | 1.010025 | 1.063483 | 1.266066 | 2.279586 | 4.880806 | 11.30219 |

| | μa | | | | | |
|---|---|---|---|---|---|---|
| | 5 | 6 | 7 | 8 | 9 | 10 |
| A(a) | 27.24293 | 67.25837 | 168.7412 | 428.3279 | 1097.086 | 2830.311 |

Evaluation of the more practical expression for absolute attenuation A, confirms the result shown in Table 2, where:

TABLE 2

$$A = \frac{I_{AV}(a)}{I_0} = \frac{1}{2\pi}\int_0^{2\pi} e^{-\mu L(1+(a/L)\sin(\tau))} d\tau$$

| μL | a/L 0 | 0.1 | 0.2 | 0.5 | 1 | Max/Min |
|---|---|---|---|---|---|---|
| 1 | 0.367879 | 0.3688 | 0.371567 | 0.391234 | 0.46576 | 1.266066 |
| 2 | 0.135335 | 0.136692 | 0.140803 | 0.171343 | 0.308508 | 2.279586 |
| 5 | 0.006738 | 0.007166 | 0.008531 | 0.022167 | 0.183561 | 27.24293 |

In some embodiments, radiation shield 102 is designed so each element 402 has a μL value of 5 and fluid 408 undergoes oscillations of amplitude a/L close to 1. In these embodiments, 18% of radiation 114 passes through radiation shield 102 and the ratio of maximum to minimum radiation allowed through (116) is higher than 25:1.

Figure 7:
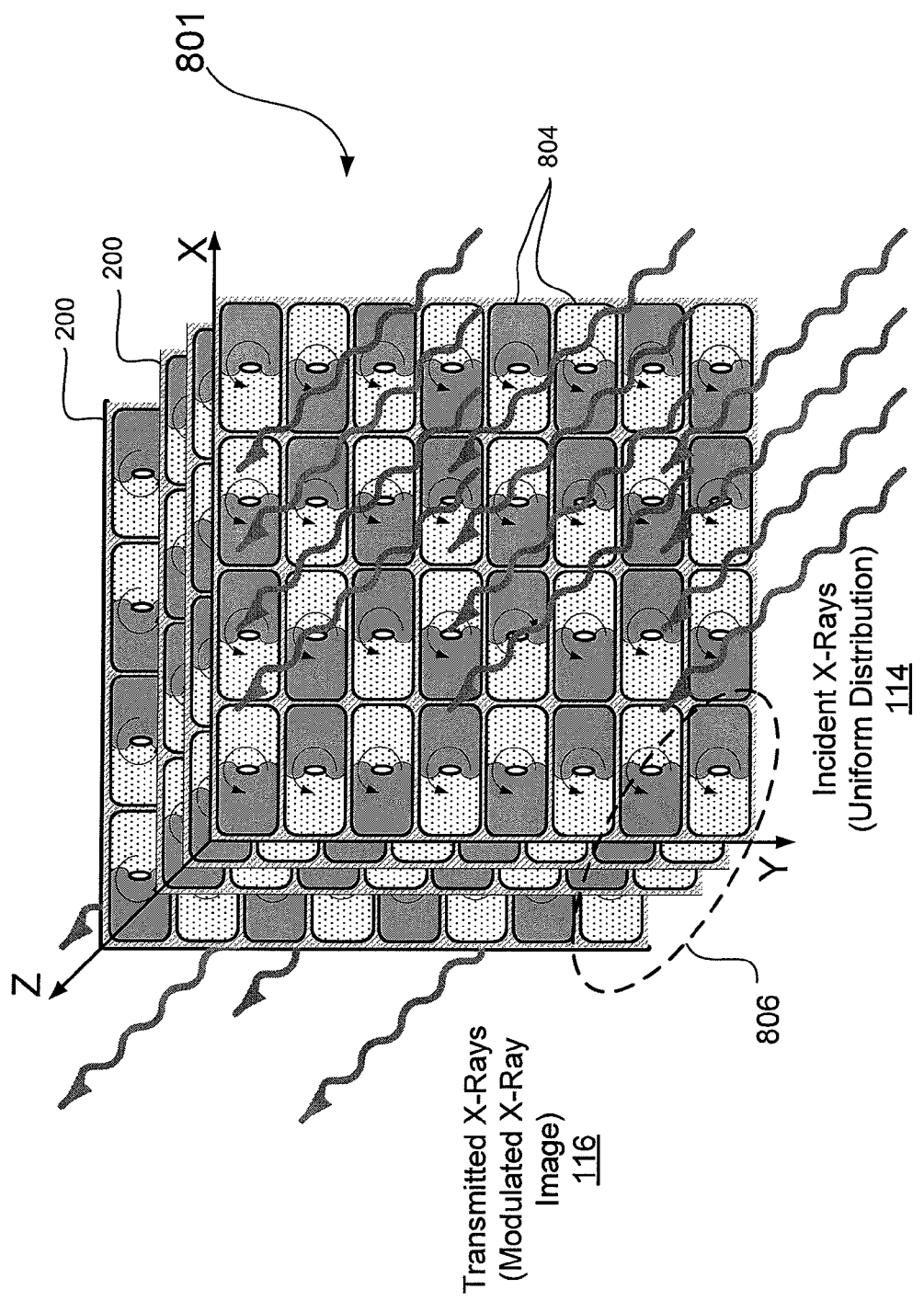
FIG. 7 illustrates another embodiment of a radiation shield comprising stacked element cells.

FIG. 7 illustrates a 3-dimensional view of an embodiment of radiation shield 801 that comprises planar arrays 200 (x-y axis), wherein multiple dual chamber cells, i.e., elements 804, are stacked 806 in a z-axis with corresponding chambers A and B precisely aligned and incident to radiation 114. Unlike element 402 of FIGS. 4A-C, a steady state configuration of elements 804 is attained when fluid 800 totally fills chamber A or chamber B. Varying degrees of radiation attenuation are achieved by alignment of precisely stacked multiple elements 804, and not by partially filling a chamber. Accordingly, incident radiation 114 of a uniform distribution incident upon the surface of any individual stack 806 is attenuated based upon the total amount of radiation attenuating fluid 800 in the z-axis, for all stacked elements 804 having the same x-y coordinate.

FIGS. 8A-8G illustrate a sequence of operational states based upon stack 806 of precisely aligned elements 804 as implemented in radiation shield 801 of FIG. 7. A radiation attenuating property of one chamber of element 804 is achieved by dynamically shifting radiation attenuating fluid 800, such as a liquid metal or a high density powder dispersed in a non-settling colloidal suspension, between chambers A and B of an elemental cell defined by an outer radiation transparent enclosure 901 and a center pivot structure 808, the pivot structure 808 operable to facilitate the controlled displacement of fluid 800. In one embodiment, fluid 800 displaces a second fluid 802, wherein fluid 802 has excellent radiation transmitting properties, such as silicone or mineral oils. In another embodiment, element 804 comprises only one fluid, radiation attenuating fluid 800.

In one embodiment, the attenuating fluid 800, when at rest, occupies at least one of the boundary regions between the chambers A and B. Furthermore, in at least one embodiment, fluid 800 is non-wetting with respect to the enclosure 901 having a sufficiently high relative surface tension to move between the chambers as a single deformable object without splitting into smaller droplets. For example, in at least one embodiment radiation attenuating fluid 800 comprises mercury.

Figure 9:
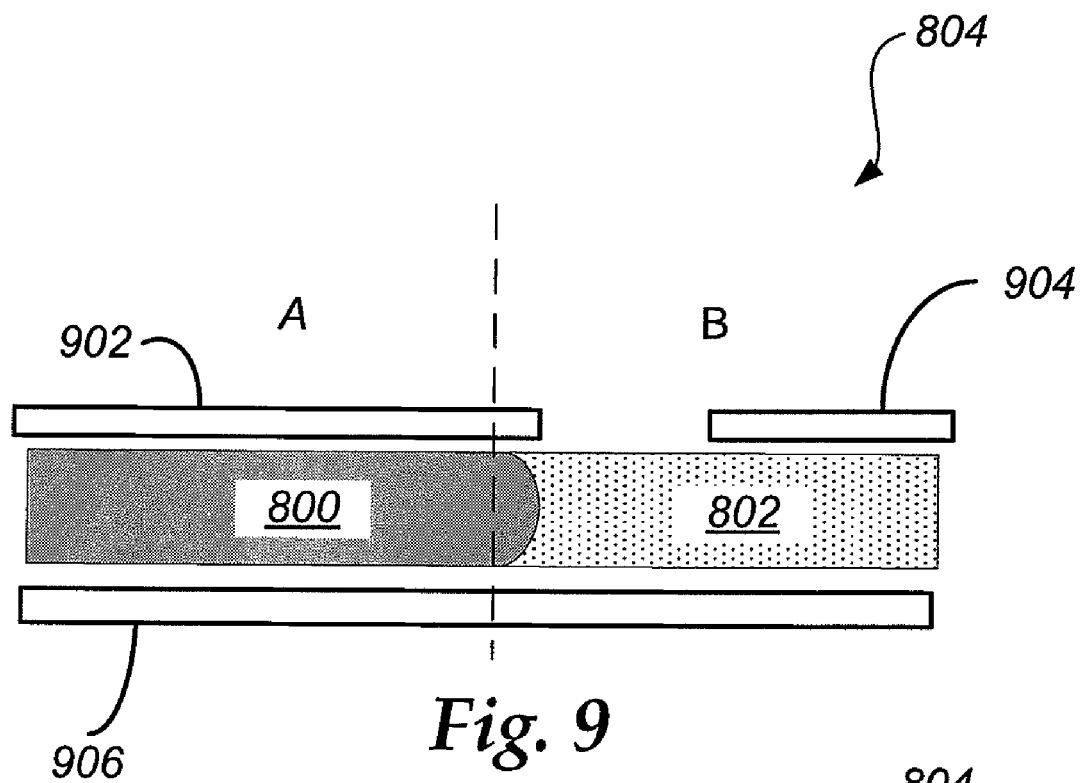
FIG. 9 is a section view taken along line 9-9 of the attenuating element of FIG. 8A.
Figure 10:
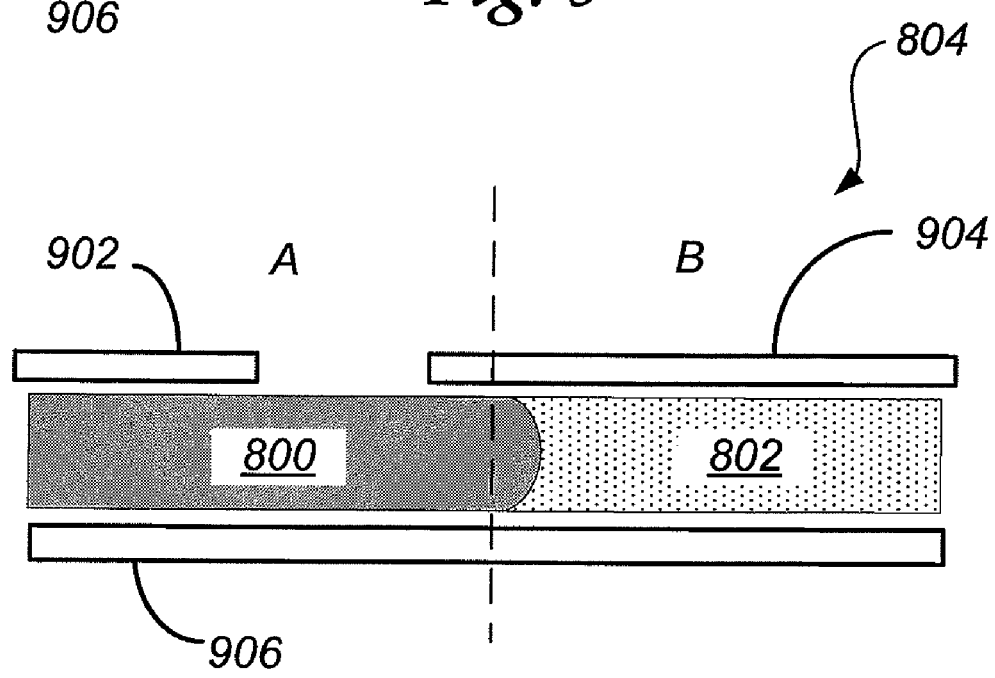
FIG. 10 is a section view taken along line 10-10 of the attenuating element of FIG. 8A.
Figure 11A:
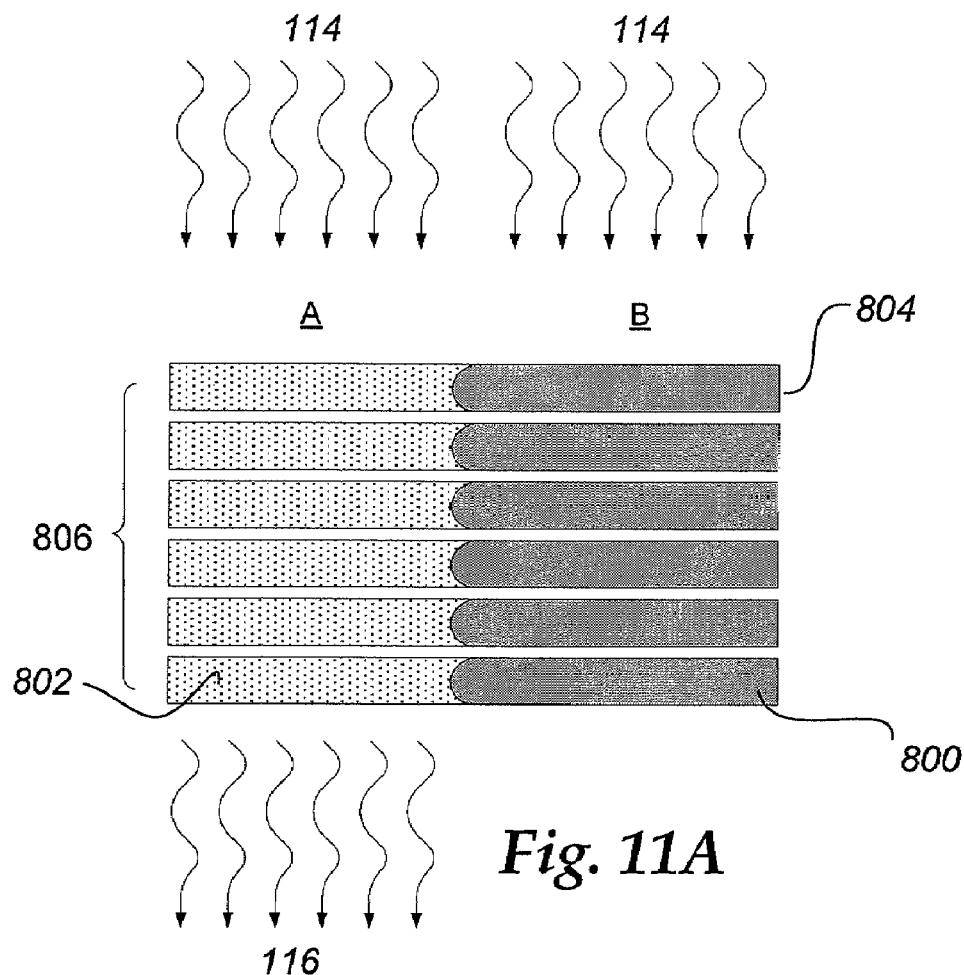
FIGS. 11A-11G illustrate elevation views of operational states of a stack of attenuating element cells, according to FIG. 7.
Figure 11B:
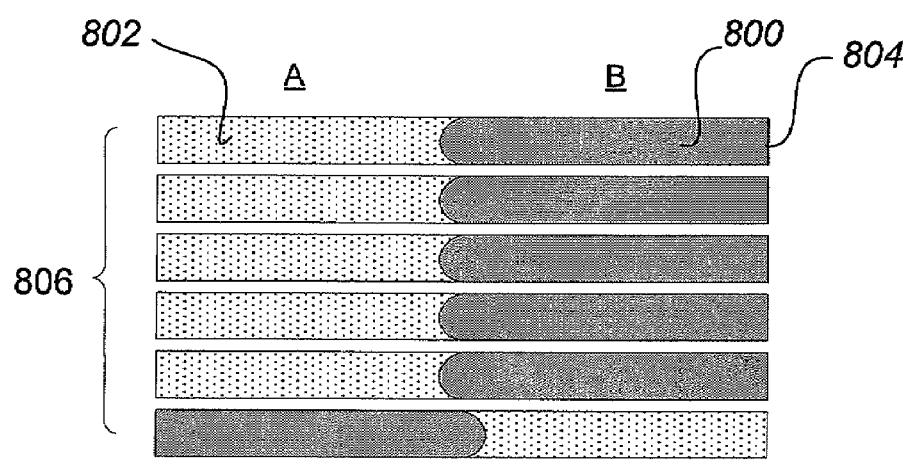
Figure 11C:
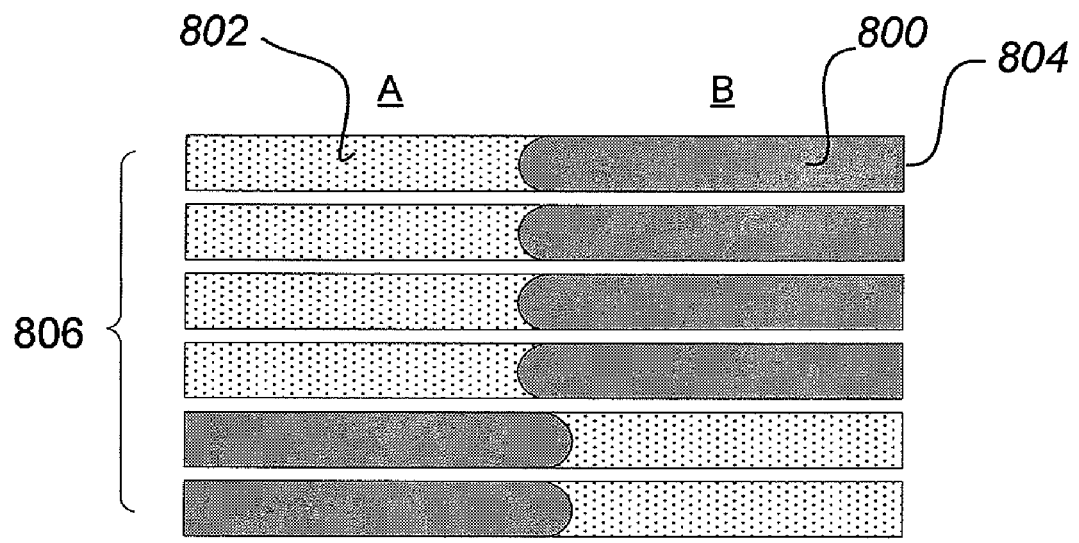
Figure 11D:
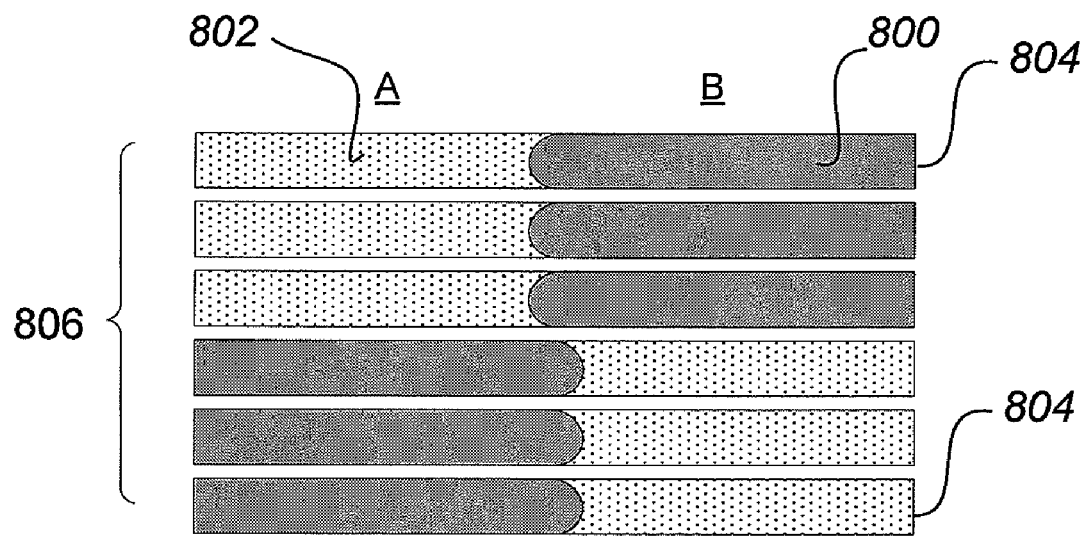
Figure 11E:
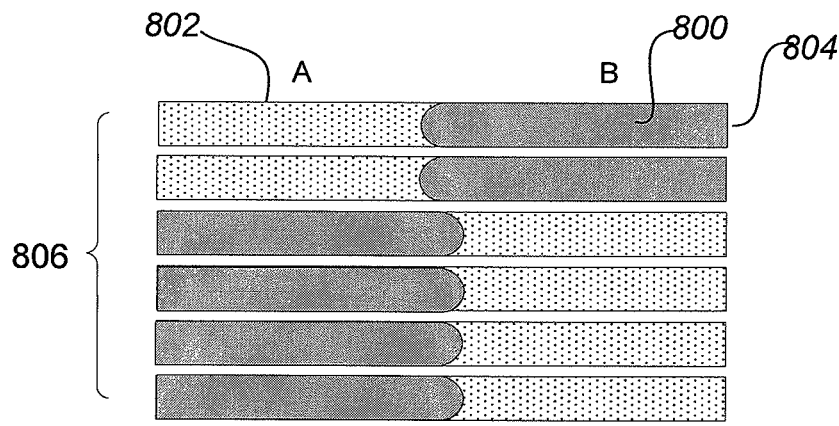
Figure 11F:
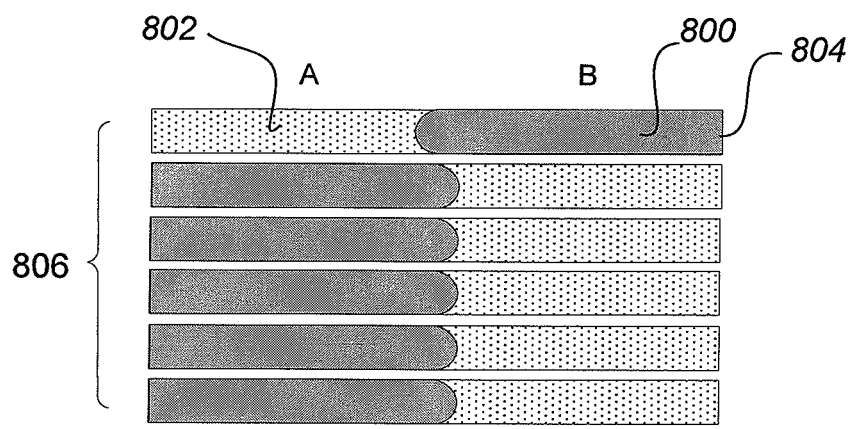
Figure 11G:
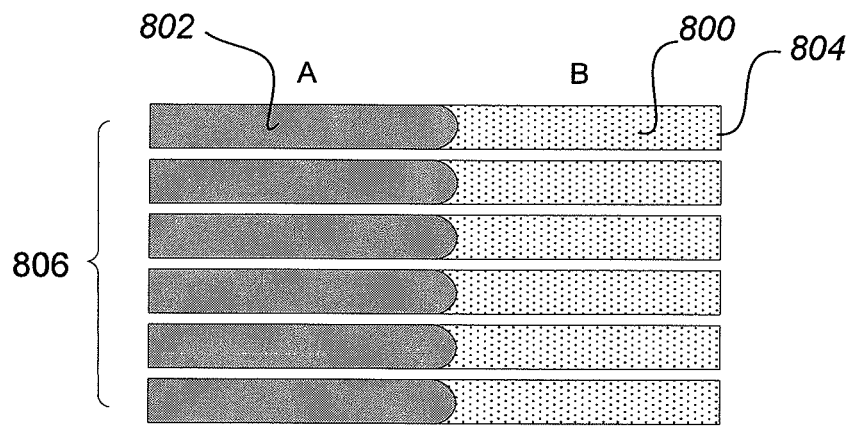

As best illustrated in FIGS. 9 and 10, each element of the stack further comprises three electrodes 902, 904, and 906, wherein electrodes 902 and 904 are on one side, i.e., an upper side, and electrode 906 is on the opposite side of element 804 across from electrodes 902 and 904, i.e., a lower side as depicted. The shape of electrodes 902, 904 is such that at least one electrode covers one of the boundaries between attenuating fluid 800 and radiation transmitting fluid 802.

Figure 8A:
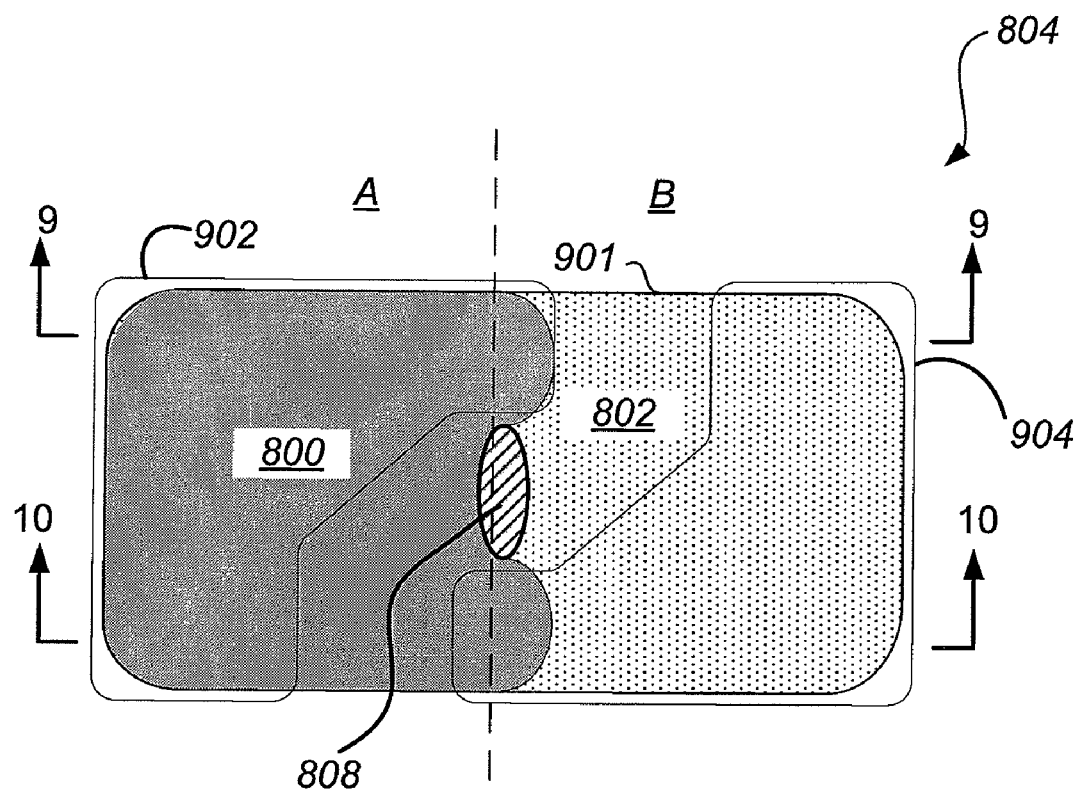
FIGS. 8A-8G illustrate top views of operational states of a radiation attenuating element according to FIG. 7.
Figure 8B:
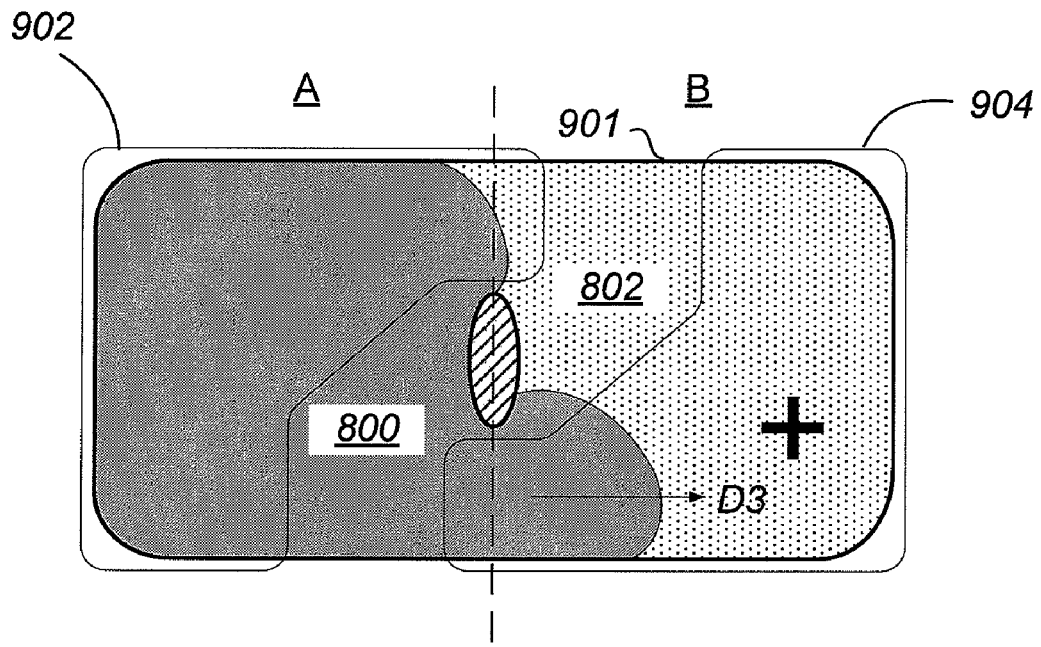
Figure 8C:
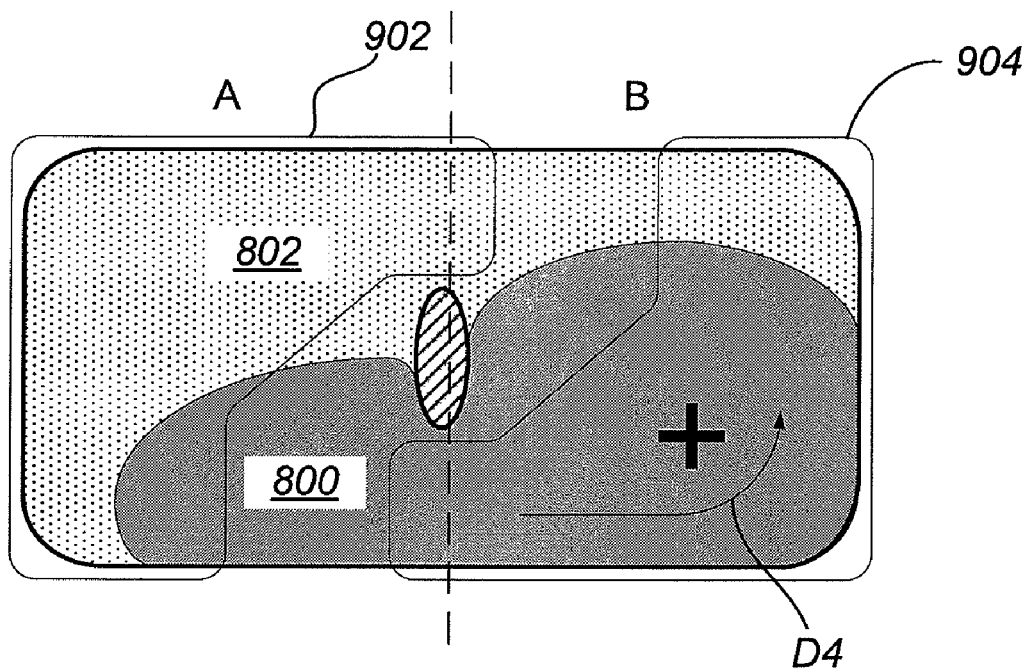
Figure 8D:
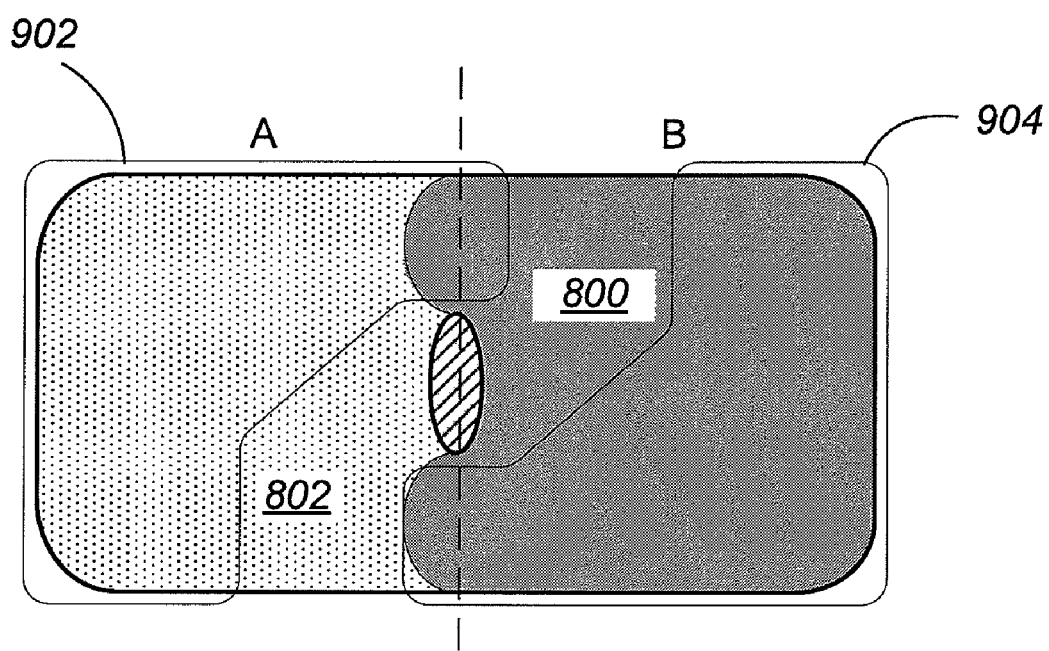

Electrode 906 covers both chambers. The sequence of states depicted in FIGS. 8A-8G illustrate the movement of radiation attenuating fluid 800 between chambers A and B. Starting with fluid 800 in chamber A (FIG. 8A) a voltage, greater or equal to threshold voltage ($V_T$), is applied between electrodes 904 and 906 (not shown), while keeping electrode 902 at the same potential as electrode 906. An electrical force then develops which attracts the fluid 800, in direction D3, to below electrode 904 in chamber B (FIG. 8B). This force may be electrostatic, dielectrophoretic or electrowetting, depending on the nature of fluid 800 and the detailed wiring of electrodes 902, 904, and 906.

During the initial part of the movement, FIG. 8B for example, surface tension of fluid 800 may oppose the external electrical force generated by electrodes 904 and 902. However, after a tipping point, the surface tension favors motion in direction D4, forcing fluid 800 to the state illustrated in FIG. 8C. Once fluid 800 is completely moved in chamber B, i.e., FIG. 8D, the external force can be removed.

Figure 8E:
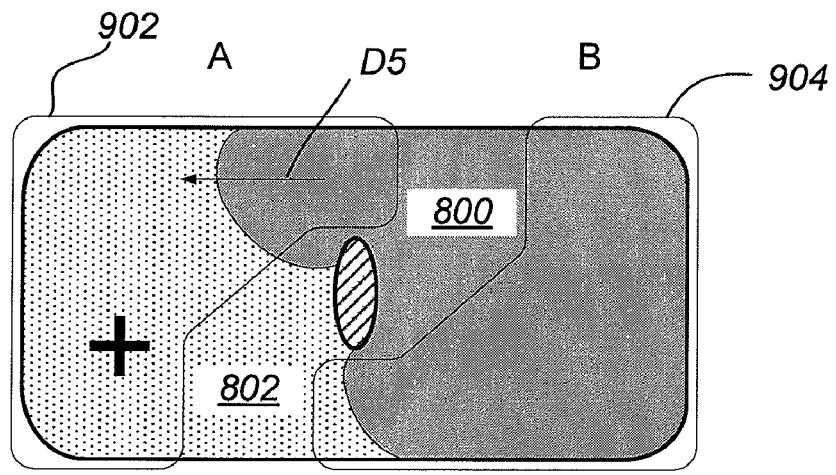
Figure 8F:
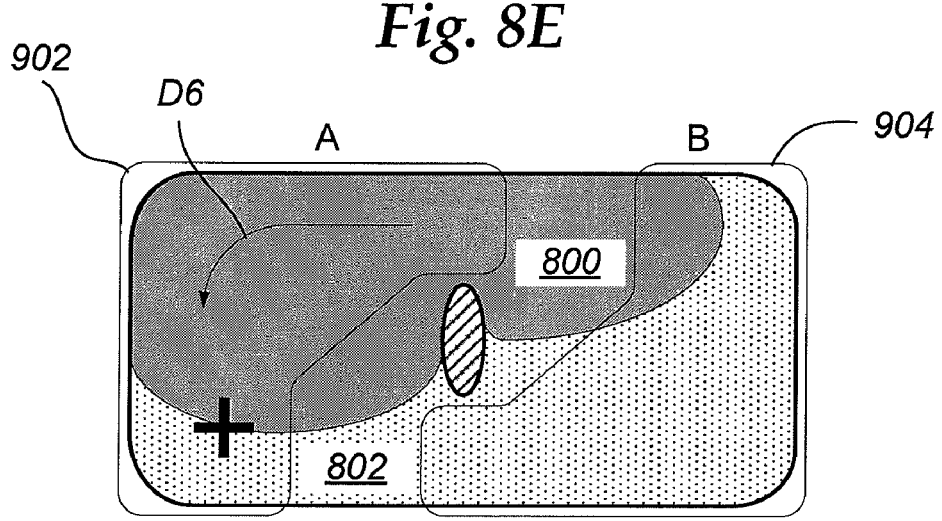
Figure 8G:
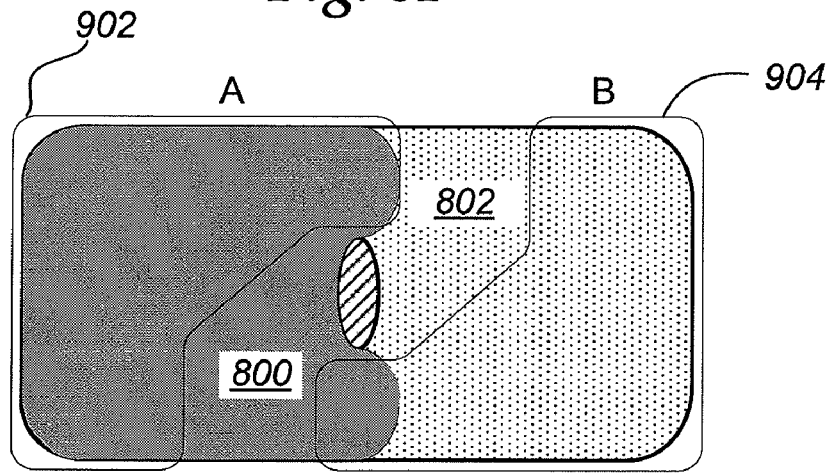

If the surface tension of fluid 800 is high enough, fluid 800 will maintain the new position despite the fluid weight. Furthermore, if a voltage potential is applied between electrodes 902 and 906, but is below a certain threshold value, the surface tension prevails and fluid 800 stays in chamber B. When the voltage between electrodes 902 and 906 exceeds the threshold voltage, fluid 800 travel back into chamber A (FIGS. 8E, 8F, and 8G). When fluid 800 is in one of the chambers A and B and fluid 802 is in the other of the chambers A and B the fluid system of the attenuation element is in a state of reduced potential energy. To toggle the fluids 800, 802 between the two chambers, the fluid system requires additional energy which may be imparted by an external actuating system. This energy is used to overcome the potential barrier between the two reduced potential energy states and which is due to the energy required to squeeze the high surface tension fluid through the channels separating chambers A and B. In another embodiment fluid 800 has low surface tension and fluid 802 has high surface tension. Still in another embodiment, fluid 802 is acted upon by electrostatic, dielectrophoretic or electrowetting forces instead of fluid 800.

The upper limit of the rotation frequency depends on the size and design of the element, the nature of the liquid, and the strength of the electrical force. For millimeter and sub-millimeter sized elements the frequency limit may range from hundreds of Hertz to a few kiloHertz.

FIGS. 11A-G illustrate various states of a stack 806 of radiation attenuating elements 804. When fluid 800 in all stacked elements 804 is positioned either in chamber A (FIG. 11A) or B (FIG. 11G) stack 806 has a maximum local opacity on the side of the fluid 800 and maximum local transparency on the opposite side. By alternately setting all elements 804 in stack 806 between the configurations shown in FIGS. 11A and 11G for an equal total time, the average overall transparency per exposure is at a maximum value, approaching 50%. When radiation attenuating liquid 800 is equally distributed among the A and B chambers (FIG. 11D) stack 806 exhibits maximum overall opacity and depends upon the nature and total thickness of the fluid (μL).

Figure 12:
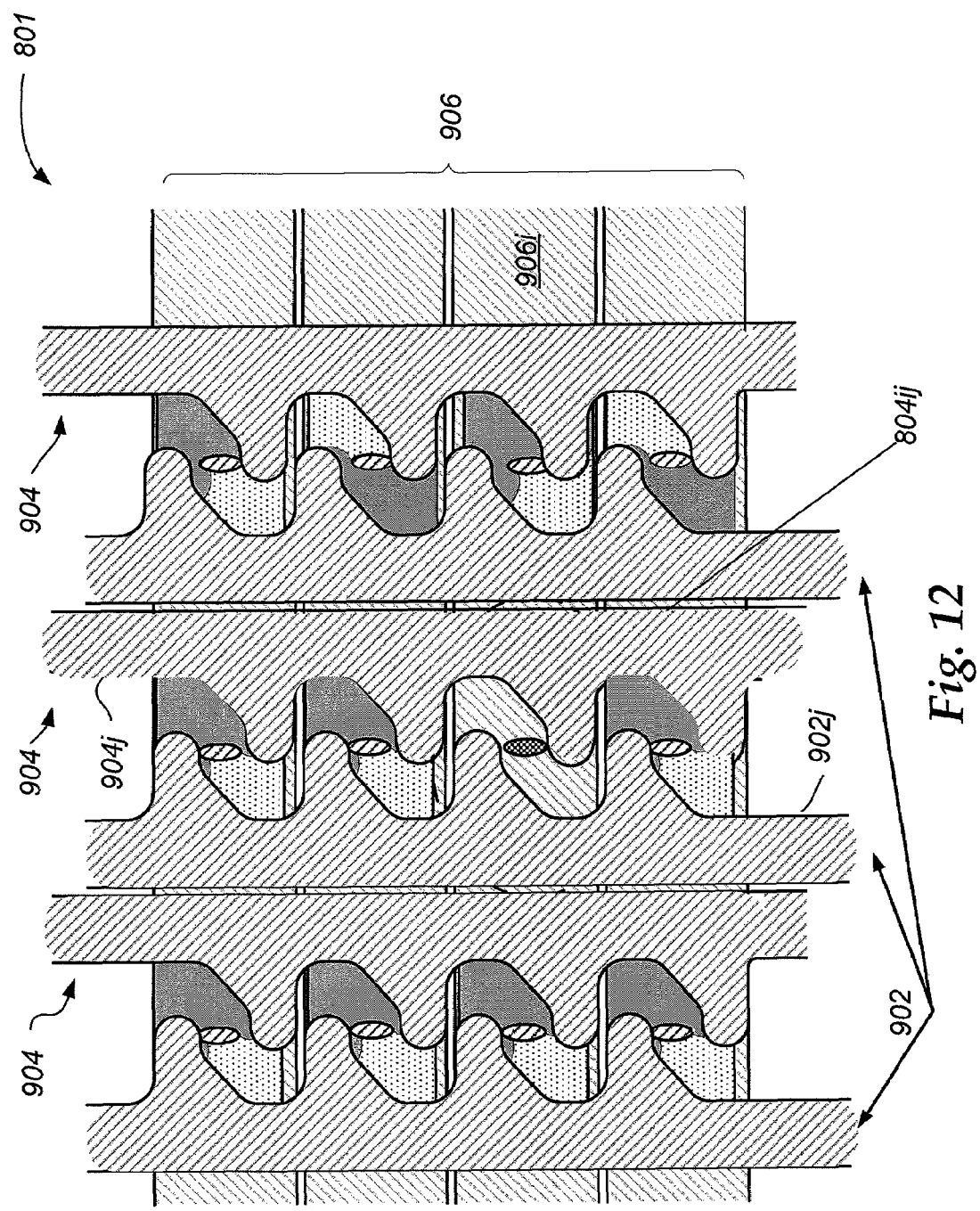
FIG. 12 illustrates an embodiment wherein an array of attenuating elements, according to FIG. 8, are electrically connected.

FIG. 12 illustrates wherein radiation shield 801 comprises a large number of element stacks 806, wherein electrodes 902, 904, and 906 are continuous segments of radiation transparent and electrically conducting film, such as indium tin oxide (ITO) or thin film metal.

The transparency to radiation property of each stack 806 is determined by how many aligned elements 804 in a stack 806 contain attenuating fluid 800 rotating synchronously between chambers A and B at a given time as compared to how many aligned elements 804 have attenuating fluid symmetrically positioned between the chambers (see FIGS. 11A-11G).

Figure 13:
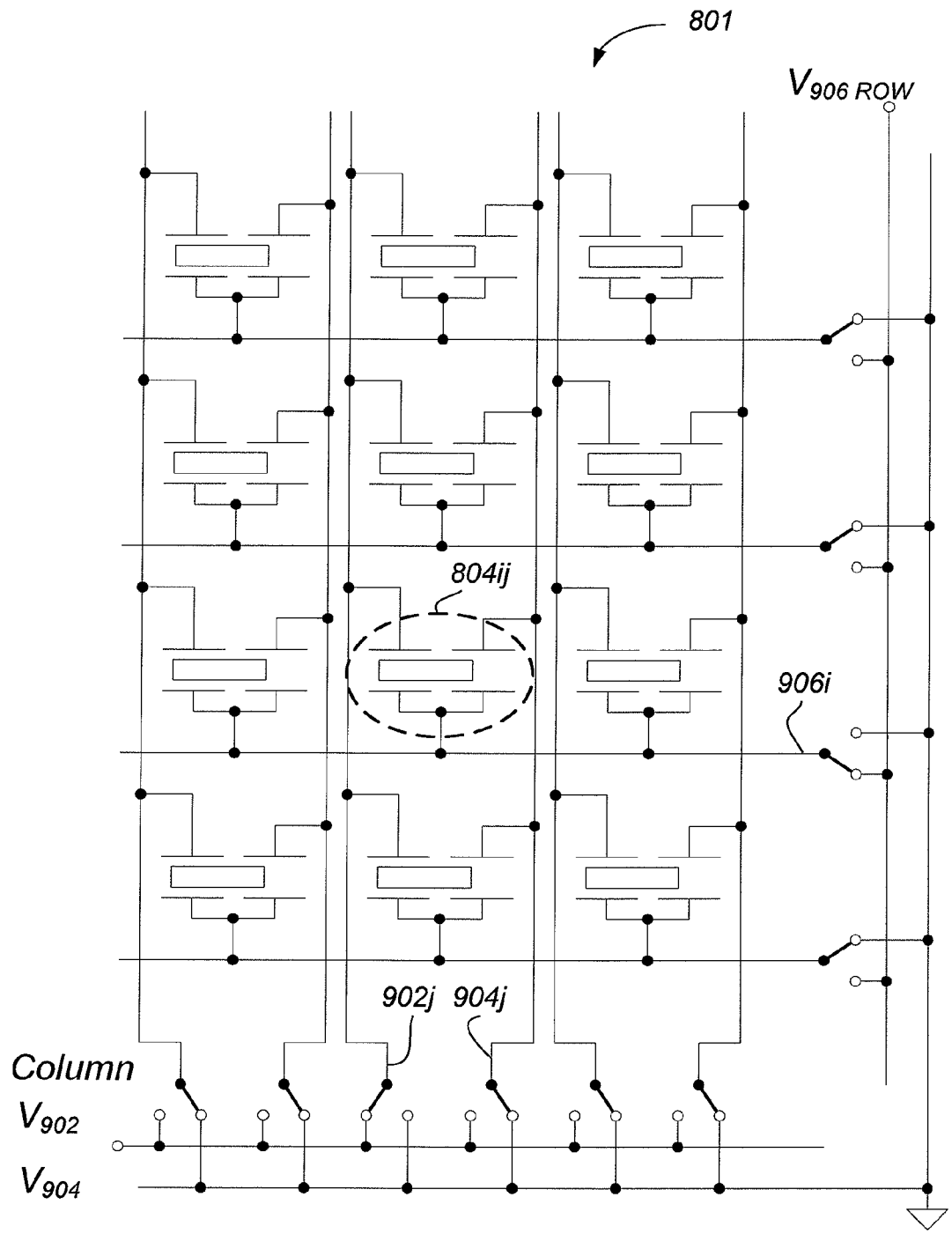
FIG. 13 illustrates row and column activation of the attenuating element array, according to FIG. 12.

Based upon a threshold value $V_T$ for toggling fluid 800, in at least one embodiment, FIG. 13 illustrates a multiplexing technique used to dynamically modulate each element 804 of radiation shield 801. In a plane comprising a two-dimensional array of elements 804, all electrodes 902 of elements 804 are disposed along a same vertical line and are connected together forming a single column electrode 902j. Similarly, all electrodes 904 located along the same vertical are connected together as 904j. However, electrodes 902 and 904 of elements 804, located in different vertical planes are electrically independent (isolated) and are driven by different column driver circuits.

All electrodes, placed along the same horizontal, i.e., 906i, are connected together and driven by the same row driver circuit. Electrodes placed along different horizontals are isolated from each other and are driven by different row driver circuits. Accordingly, a voltage potential larger than $V_T$ applied between an electrode column (902j) and electrode row (906i) will cause fluid 800 in element 804ij, located at the intersection of electrode column (902j) and electrode row (906i), to move underneath the electrode 902 of element 804ij.

A maximum voltage $V_T$ is determined to avoid a situation in which even if all unselected rows and columns are grounded, a force present in nearby elements may be sufficient to cause fluid 800 to move in undesired elements along the 902j and/or 906i path.

A voltage scheme that avoids such undesirable movement includes using voltage levels for column and row voltages which satisfy the conditions:

$$V_T/2 < V_{COLUMN} < V_T$$

$$-V_T/2 > V_{ROW} > -V_T$$

Accordingly, voltages $V_{902j}$ and $V_{906i}$ are set below a threshold voltage capable of toggling attenuating fluid 800 along the 902j and 906i paths, except at the desired element where they intersect at element 804ij.

Driving Voltage Determination

Figure 14:
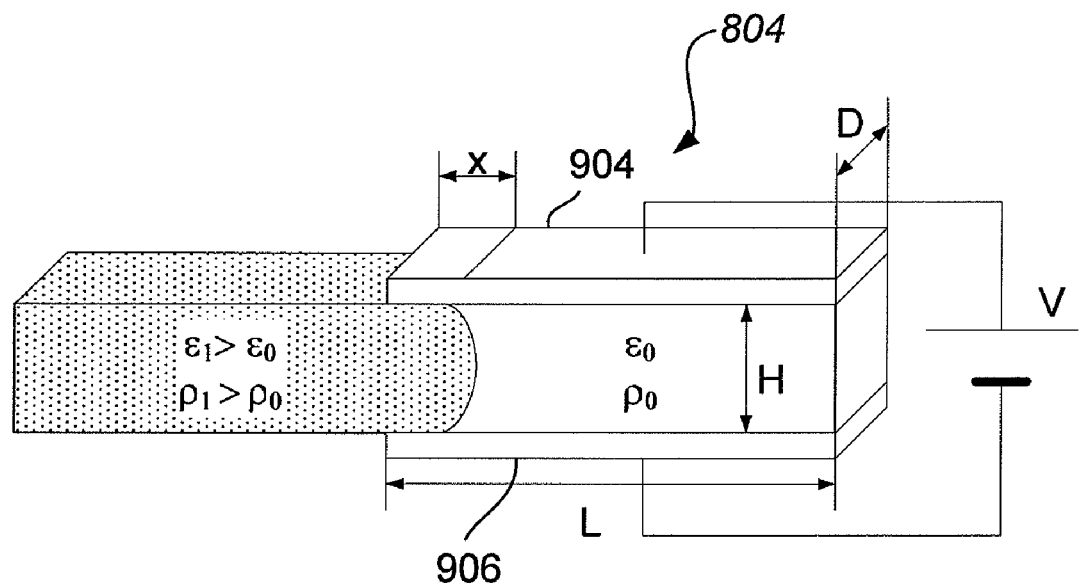
FIG. 14 illustrates one embodiment of an apparatus that drives the attenuating element according to FIG. 7.

FIG. 14 illustrates one embodiment that generates a force capable of driving fluid 800 between chambers A and B of an element 804. In one embodiment, the driving force is electrostatic and attenuating fluid 800 is an insulator liquid having a permittivity $\in_1$ that is different than permittivity $\in_0$ of radiation transmitting fluid 802. FIG. 14 illustrates schematically, the equivalent capacitor formed by electrodes 904 and 906 (see FIG. 10) of chamber B and which overlaps the interface between fluids 800 and 802. A similar arrangement governs the actuation of fluid 800 in chamber A.

The general expression for the capacitance of a planar electrode capacitor is given by:

$$C = \frac{\varepsilon S}{H}$$

where S is the area of the electrodes, H is the separation between electrodes and $\in$ is the permittivity of the material between the electrodes.

For the compound capacitor of FIG. 14:

$$C = \frac{\varepsilon_1 Dx}{H} + \frac{\varepsilon_0 D(L-x)}{H}$$

$$C = \frac{\varepsilon_0 DL + xD(\varepsilon_1 - \varepsilon_0)}{H}$$

The energy stored by this capacitor is:

$$E = \frac{CV^2}{2}$$

where V is the voltage applied between the electrodes 904 and 906.

If $\in_1 > \in_0$ then by applying a voltage across the capacitor plates an electrostatic force develops at the boundary between attenuating fluid 800 and radiation transmitting fluid 802 which tends to move the fluid 800 between the plates. The absolute value of this force is:

$$F_E = \frac{dE}{dx} = \frac{V^2}{2}\frac{dC}{dx} = \frac{V^2 D(\varepsilon_1 - \varepsilon_0)}{2H}$$

Because the radiation shield 801 may positioned horizontally, vertically, or at any angle in between, the driving electrical force must be sufficient to lift the working liquid against gravity (dead weight lift), such that:

$$F_E > F_G$$

When $F_G$ is such that:

$$F_G = HDLg(\rho_1 - \rho_0)$$

inequality $F_E > F_G$ reduces to:

$$\frac{V^2 D(\varepsilon_1 - \varepsilon_0)}{2H} > HDLg(\rho_1 - \rho_0)$$

Solving for driving voltage V results in:

$$V > \sqrt{\frac{2H^2 Lg(\rho_1 - \rho_0)}{(\varepsilon_1 - \varepsilon_0)}}$$

In one embodiment wherein $\in_1 - \in_0 = 5 \times 10^{-11}$ F/m:

$\rho_1 > \rho_0 = 5 \times 10^3$ Kg/m$^3$ $g = 9.81$ m/s$^2$ $H = 10^{-4}$ m $L = 10^{-3}$ m the required voltage V is calculated to be:

V>140V which is well within the capabilities of high voltage multi-channel driver circuits, such as those used to drive electrostatic printers and electroluminescent displays.

Figure 15:
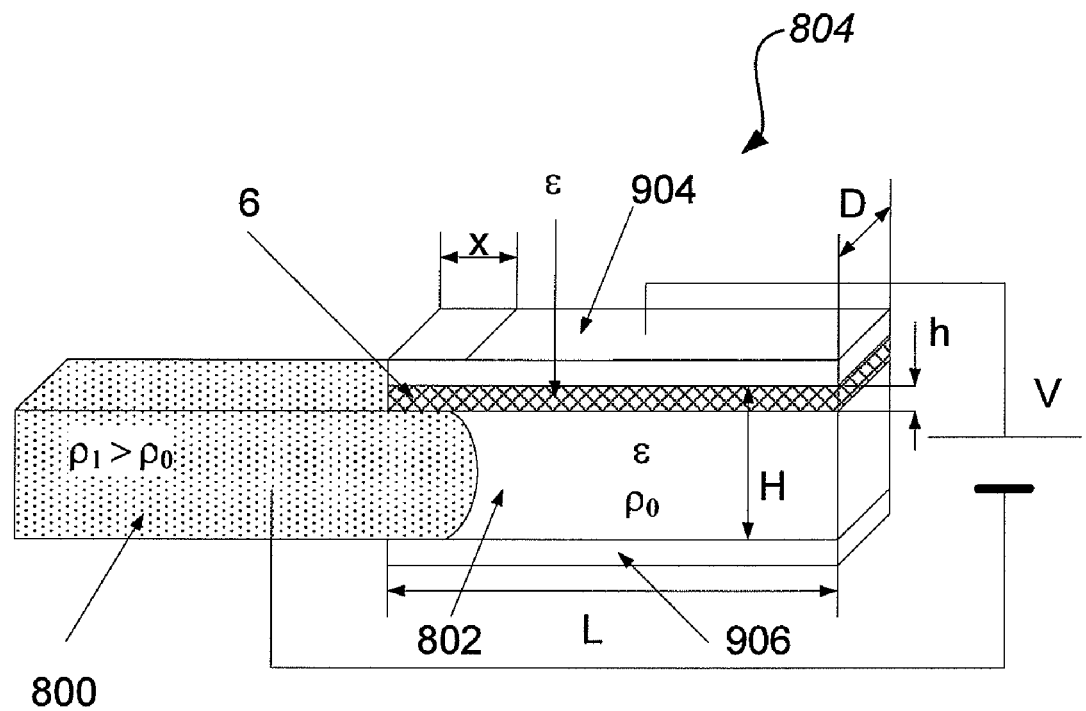
FIG. 15 illustrates another embodiment of an apparatus that drives the attenuating element according to FIG. 7.

FIG. 15 illustrates one embodiment of an element 804 that uses electro-wetting as a drive force. As illustrated, fluid 800 is conductive and in electrical and mechanical contact with electrode 906. A thin dielectric film 6 electrically insulates fluid 800 from electrode 904. When a potential V is applied between fluid 800 and electrode 904, fluid 800 is attracted along the surface of film 6, the bulk of fluid 800 moving as one integral element due to surface tension forces.

The compound capacitance measured between electrodes 904 and 906 is then approximately:

$$C = \frac{\varepsilon Dx}{h} + \frac{\varepsilon D(L-x)}{H}$$

$$C = \frac{\varepsilon DL}{H} + \varepsilon Dx\left(\frac{1}{h} - \frac{1}{H}\right)$$

The electro-wetting force is given by:

$$F_E = \frac{dE}{dx} = \frac{V^2}{2}\frac{dC}{dx} = \frac{V^2 \varepsilon D(H-h)}{2hH}$$

And finally the drive voltage V is given by:

$$V > \sqrt{\frac{2hH^2 Lg(\rho_1 - \rho_0)}{\varepsilon(H-h)}}$$

In one exemplary embodiment wherein $\in = 5 \times 10^{-11}$ F/m, and fluids 800 and 802 are water and air, respectively:

$\rho_1 - \rho_0 = 10^3$ Kg/m$^3$ $g = 9.81$ m/s$^2$ $H = 10^{-4}$ m $h = 10^{-5}$ m $L = 10^{-3}$ m Based upon the drive voltage formula above, V>20 V.

In another embodiment of the element cell, wherein fluid 800 is mercury:

$\in = 10^{-10}$ F/m $\rho_1 - \rho_0 = 13 \times 10^3$ Kg/m$^3$ $g = 9.81$ m/s$^2$ $H = 3 \times 10^{-4}$ m $h = 10^{-5}$ m $L = 3 \times 10^{-3}$ m Solving for the driving voltage, V>450 V, which is still in the range of known driver electronics. In still other embodiments, the use of very high permittivity materials for the dielectric film, such as compounds of barium titanate, may lower the actuation voltage to less than 20 V.

Figure 16:
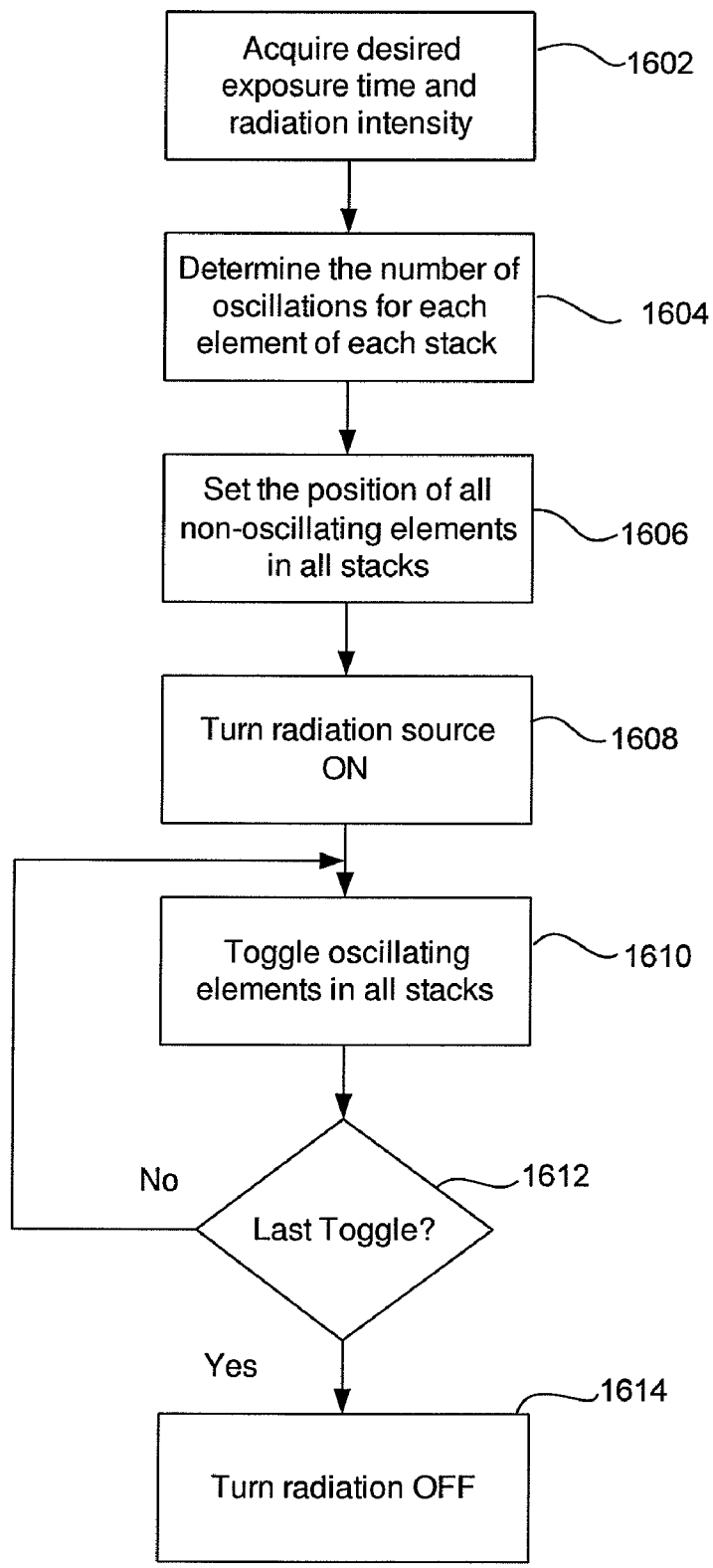
FIG. 16 illustrates a flowchart illustrating one embodiment of a method of dynamically modulating radiation, according to the radiation imaging system of FIG. 1.

FIG. 16 illustrates a flowchart of one embodiment of imaging system 100 based upon radiation shield 801 (see FIGS. 1 and 7), to dynamically modulate the attenuation property of radiation shield 102. The method includes acquiring desired exposure time and radiation intensity (1602). This value may be entered by an operator using input device 216.

Executing logic 214, processor 202 determines (1604) the number of oscillations for each element 804 of each stack 806.

After determining the number of oscillations, non-oscillating elements 804 in stacks 806 is selected by appropriate setting (1606) of row and column voltages logic 214, as illustrated in FIG. 13.

After setting (1606) the attenuating property of each of the elements 804 of the radiation shield 801, a source 110 of radiation 114 is turned on (1608) to irradiate target 118 with radiation 116 that has been attenuated by radiation shield 801. After a predetermined amount of time, the attenuating fluid 800 in each element 804 of stack 806 is toggled (1610) between chambers A and B. Based upon the predetermined number of oscillations, functional block 1610 is repeated. After determining at block 1612 that all oscillations have been performed, the radiation source 110 is turned off (1614).

Figure 17:
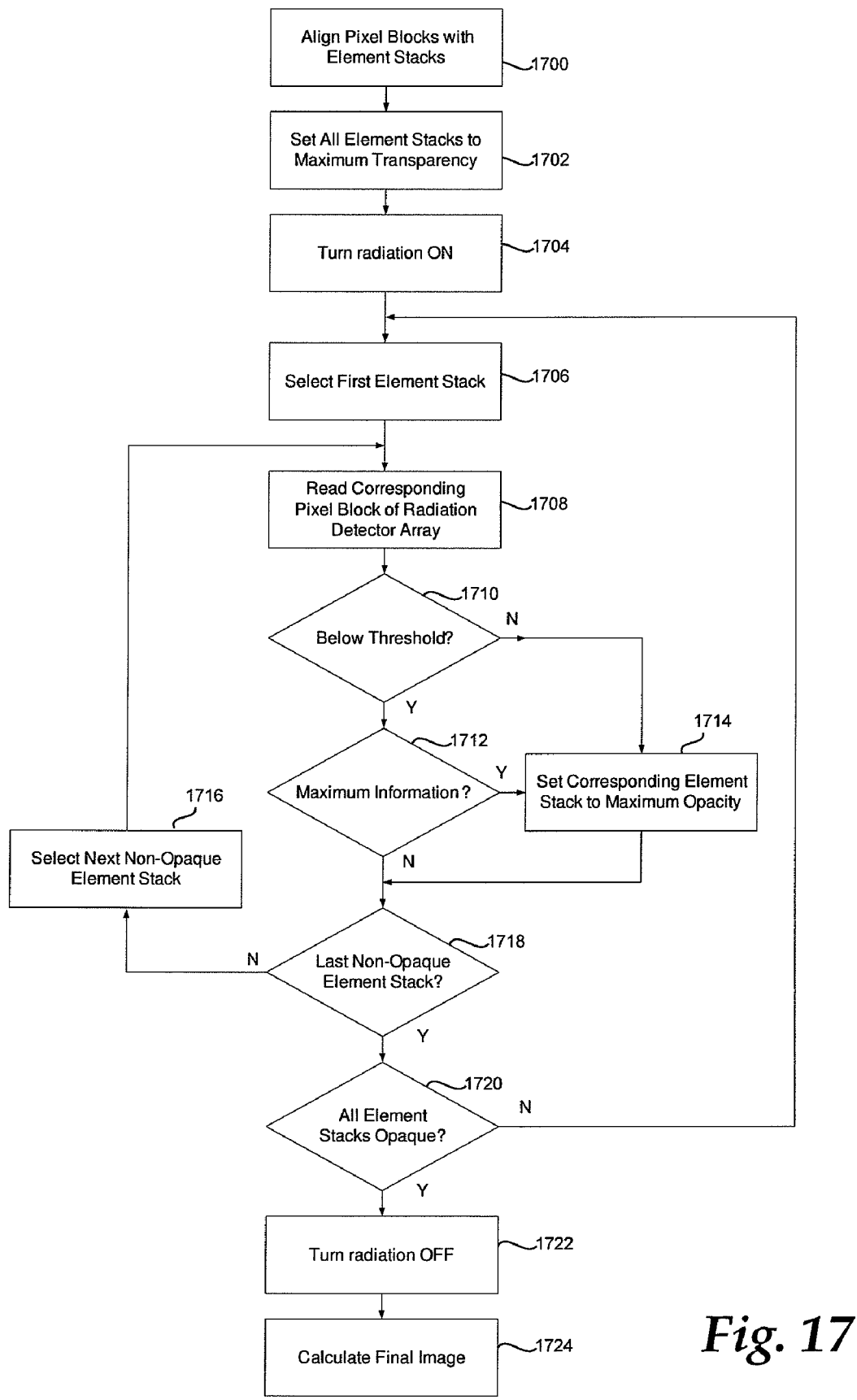
FIG. 17 illustrates s flowchart illustrating another embodiment of a method of dynamically modulating radiation, using the radiation imaging system of FIG. 1.

FIG. 17 illustrates a flowchart of one embodiment of a method to dynamically modulate the attenuation property of radiation shield 102, according to the system in FIG. 1, wherein radiation shield 102 comprises a plurality of stacked elements 804, as disclosed in radiation shield 801 of FIG. 7.

During alignment stage 1700, all individual elements 804 of stacks 806 are turned ON and OFF, the radiation source 110 is turned ON and OFF and each block of pixels in detector array 106 in the shadow of each element stack 806 is mapped. The patient 118 is then positioned, all the element stacks 806 are set to maximum transparency (1702) and exposure commences (1704).

The cumulative amount of radiation passing through the first element stack is calculated (1706), and a determination is made (1708), (1710) whether the cumulative amount of radiation is above a safe predetermined threshold. If above, the element stack is set to maximum opacity (1714). If not, the information density of the corresponding pixel block is read and evaluated At block 1712, a determination is made whether the maximum amount of information has been collected out of the current pixel block, that is, whether additional exposure to radiation will reduce the information content of the pixel block, resulting in partial or total detector saturation. If an optimal exposure has been achieved, the corresponding element stack 806 is set to maximum opacity (1714). If additional exposure is warranted, exposure continues through the current element stack and the next element stack is selected for processing (1716).

If the current pixel block corresponds to the last element stack of the radiation shield 801 (1718) and if there are non-opaque element stacks remaining, the process is repeated (1720) starting with the first element stack at block 1706. If all cell stacks have been rendered opaque, the radiation source 110 is turned OFF (1722) and the image, generated by detector array 106 and control unit 104 is processed (1724) to remove non-uniformities due to the fact that different pixel blocks were exposed for different amounts of time. Because local exposure is limited only to the time required to obtain maximum information out of any given target area, the total amount of radiation absorbed by the patient is greatly reduced.

Other operational modes include pre-procedure computer controlled collimation of radiation, dynamic re-collimation during procedures, gray level operation (different element stacks have different levels of transparency) and other which may be familiar to those skilled in the art.

The various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Further, the steps and/or actions of the method or algorithm described in connection with the aspects disclosed herein may be embodied directly in hardware, in a software module executed by a processor, or in a combination of the two. While the foregoing disclosure shows illustrative aspects and/or embodiments, it should be noted that various changes and modifications could be made herein without departing from the scope of the described aspects and/or embodiments as defined by the appended claims. Furthermore, although elements of the described embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

What is claimed is:

1. A radiation attenuating device, comprising:
at least two directly communicating adjacent chambers;
at least one communication channel connecting the chambers;
at least one fluid, wherein one of the at least one fluid is a radiation attenuating fluid moveable between the chambers; and
a control circuit configured to oscillate the radiation attenuating fluid between the chambers.

2. The radiation attenuating device according to claim 1, wherein a height of the radiation attenuating fluid in each chamber is varied by moving a portion of the fluid from one chamber to another chamber through the communicating channel.

3. The radiation attenuating device according to claim 1, wherein an amount of time the radiation attenuating fluid resides in any one chamber is smaller than an exposure time to radiation incident to the chamber.

4. The radiation attenuating device according to claim 1, wherein the radiation attenuating fluid is one of liquid metal or a high density powder dispersed in a non-settling colloidal suspension.

5. The radiation attenuating device according to claim 1, wherein each chamber comprises a shape such that an occupying fluid is in a reduced potential energy state.

6. The radiation attenuating device according to claim 1, wherein the at least one communication channel between the adjacent chambers comprises at least one potential energy barrier for at least one of the fluids.

7. The radiation attenuating device according to claim 1, further comprising:
at least one operational state wherein a volume of the radiation attenuating fluid at least fills the volume of one of the adjacent chambers.

8. The radiation attenuating device according to claim 1, further comprising:
a radiation transparent fluid directly moveable between the adjacent chambers such that movement of one of the fluids displaces the other fluid; and
wherein a total volume of the chambers is filled by the radiation attenuating fluid and the radiation transparent fluid.

9. The radiation attenuating device according to claim 8, wherein the at least one communication channel includes a first channel configured to transport one of the fluids from a first chamber directly to a second chamber, and a second channel configured to transport the other fluid from the second chamber directly to the first chamber.

10. The radiation attenuating device according to claim 8, wherein the radiation attenuating fluid comprises a property of high surface tension and acts as a single deformable object.

11. The radiation attenuating device according to claim 8, further comprising a control circuit that includes at least three electrodes essentially transparent to radiation, the electrodes configured to have a voltage potential applied across at least two of the electrodes.

12. The radiation attenuating device of claim 11 wherein the control circuit controlling each chamber further comprises a dielectric material layer placed between one of the electrodes and the chamber, the dielectric material being of high electric permittivity and essentially transparent to radiation.

13. The radiation attenuating device of claim 11 wherein at least one of the electrodes overlaps a boundary between the two fluids when the fluids are at rest.

14. The radiation attenuating device of claim 12 wherein the dielectric material layer comprises a barium titanate compound.

15. The radiation attenuating device according to claim 1, wherein one of the fluids has different electric properties than the other fluid.

16. The radiation attenuating device according to claim 15, wherein the different electrical properties are one of a group of properties comprising electric permittivity and electric conductivity.

17. The radiation attenuating device of claim 1, wherein a plurality of the radiation attenuating devices are abutted together, forming a two-dimensional x-y array of individually controlled radiation attenuating devices.

18. The radiation attenuating device of claim 1, wherein a radiation shield is formed of multiple two-dimensional arrays of radiation attenuating devices stacked in a z-axis to form a three-dimensional matrix, wherein a stack of radiation attenuating devices in the z-axis are aligned in a substantially overlapping mode and are configured to impede the progress of incident radiation in a cumulative manner.

19. A radiation imaging system configured to dynamically modulate an amount of radiation incident to a target to be radiated, comprising:
a radiation source;
a radiation shield further comprising a plurality of radiation attenuating devices, each radiation attenuating device comprising:
a dynamically configurable radiation attenuating property;
at least two directly communicating adjacent chambers;
at least one communication channel directly connecting the adjacent chambers;
a radiation attenuating fluid directly moveable between the adjacent chambers; and
a control unit configured to generate at least one control signal to each radiation attenuating device, the control signal operable to oscillate the radiation attenuating fluid between the directly communicating adjacent chambers.

20. A radiation imaging system, according to claim 19, further comprising:
a radiation detection array in electrical communication with the control unit and configured to generate an output signal received by the control unit;
wherein the control unit is configured to dynamically modulate the radiation attenuating property of each radiation attenuating device based upon the received output signal generated by the radiation detection array.

21. A method of attenuating radiation incident to a radiation attenuating element, the method comprising:
oscillating at least one fluid between at least two directly communicating adjacent chambers, the at least one fluid having a radiation attenuating property.

22. The method of claim 21, wherein oscillating at least one fluid comprises:
exchanging a radiation transmitting fluid in one of the two directly communicating adjacent chambers with a radiation attenuating fluid in the second chamber in a time shorter than a radiation exposure time.

23. The method of claim 21, wherein oscillating the at least one fluid comprises generating a force based on at least one of electric, magnetic, electro-phoretic, dielectric-phoretic, electro-wetting, and magnetic-hydro-dynamic principles.

24. The method of claim 21, further comprising:
stacking a plurality of the radiation attenuating elements in a z-axis;
oscillating the at least one fluid between the directly communicating adjacent chambers of a radiation attenuating element in a predetermined number of stacked radiation attenuating elements whereby a total amount of radiation that is blocked is based upon a total amount of fluid incident to radiation at any one time.

* * * * *